(12) United States Patent
Foster et al.

(10) Patent No.: US 10,379,030 B2
(45) Date of Patent: Aug. 13, 2019

(54) PARTICLE MANIPULATION SYSTEM WITH CAMERA CONFIRMATION

(71) Applicant: Owl biomedical, Inc., Goleta, CA (US)

(72) Inventors: John S Foster, Santa Barbara, CA (US); Kevin E. Shields, Santa Barbara, CA (US); Mehran R. Hoonejani, Goleta, CA (US); Mark A. Naivar, Goleta, CA (US); Yareeve Zemel, Santa Barbara, CA (US)

(73) Assignee: Owl biomedical, Inc., Goleta, CA (US)

( * ) Notice: Subject to any disclaimer, the term of this patent is extended or adjusted under 35 U.S.C. 154(b) by 34 days.

(21) Appl. No.: 15/242,693

(22) Filed: Aug. 22, 2016

(65) Prior Publication Data
US 2016/0377525 A1    Dec. 29, 2016

Related U.S. Application Data

(60) Continuation-in-part of application No. 14/947,947, filed on Nov. 20, 2015, now Pat. No. 9,446,435,
(Continued)

(51) Int. Cl.
*G01N 15/14* (2006.01)
*B07C 5/342* (2006.01)
(Continued)

(52) U.S. Cl.
CPC .... *G01N 15/1463* (2013.01); *B01L 3/502761* (2013.01); *B07C 5/3425* (2013.01);
(Continued)

(58) Field of Classification Search
CPC ....... G01N 15/1459; G01N 2015/1081; G01N 2015/149
See application file for complete search history.

(56) References Cited

U.S. PATENT DOCUMENTS 5,837,200 A * 11/1998 Diessel ............. B01L 3/502761
                                                      209/155
9,404,838 B2    8/2016 Foster et al.
(Continued)

FOREIGN PATENT DOCUMENTS

WO    WO 2006/076567    7/2006
WO    WO 2008/130977    10/2008

OTHER PUBLICATIONS

U.S. Appl. No. 13/998,095, filed Oct. 1, 2013, Foster et al.
(Continued)

*Primary Examiner* — Jill A Warden
*Assistant Examiner* — Brittany I Fisher
(74) *Attorney, Agent, or Firm* — Jaquelin K. Spong

(57) ABSTRACT

A MEMS-based particle manipulation system which uses a particle manipulation stage and optical confirmation of the manipulation. The optical confirmation may be camera-based, and may be used to assess the effectiveness or accuracy of the particle manipulation stage. In one exemplary embodiment, the particle manipulation stage is a microfabricated, fluid valve, which sorts a target particle from non-target particles in a fluid stream. The optical confirmation stage is disposed in the microfabricated fluid channels at the input and output of the microfabricated sorting valve. The laser interrogation regions may be used to assess the effectiveness or accuracy of the sorting, and to control or adjust sort parameters during the sorting process.

19 Claims, 15 Drawing Sheets

Related U.S. Application Data which is a division of application No. 13/507,830, filed on Aug. 1, 2012, now Pat. No. 9,194,786.

(51) Int. Cl.
*G01N 15/10* (2006.01)
*B01L 3/00* (2006.01)

(52) U.S. Cl.
CPC ..... *G01N 15/1404* (2013.01); *G01N 15/1425* (2013.01); *G01N 15/1434* (2013.01); *G01N 15/1459* (2013.01); *G01N 15/1484* (2013.01); *B01L 2200/0636* (2013.01); *B01L 2200/0652* (2013.01); *B01L 2300/0816* (2013.01); *B01L 2300/0864* (2013.01); *B01L 2400/0454* (2013.01); *G01N 2015/1006* (2013.01); *G01N 2015/1081* (2013.01); *G01N 2015/149* (2013.01); *G01N 2015/1413* (2013.01)

(56) References Cited

U.S. PATENT DOCUMENTS

| | | |
|---|---|---|
| 2001/0055812 A1 | 12/2001 | Mian |
| 2003/0007894 A1* | 1/2003 | Wang .................. B07C 5/34 422/82.05 |
| 2003/0153085 A1* | 8/2003 | Leary .................. G01N 15/14 436/63 |
| 2005/0207940 A1* | 9/2005 | Butler ............... B01L 3/502761 422/73 |
| 2007/0178529 A1* | 8/2007 | Breidford ............ B01F 11/04 435/7.1 |
| 2010/0225913 A1 | 9/2010 | Trainer |
| 2010/0232675 A1* | 9/2010 | Ortyn .................. G01N 15/147 382/134 |
| 2012/0122084 A1 | 5/2012 | Wagner et al. |
| 2012/0190104 A1* | 7/2012 | Foster ............... B01L 3/502738 435/288.7 |
| 2012/0190105 A1 | 7/2012 | Foster et al. |
| 2012/0196314 A1 | 8/2012 | Nawaz et al. |
| 2015/0093810 A1 | 4/2015 | Foster et al. |

OTHER PUBLICATIONS

U.S. Appl. No. 13/998,096, filed Oct. 1, 2013, Foster et al.
Xiaole Mao, et al. "Single-layer planar on-chip flow cytometer using microfluidic drifting based three-dimensional (3D) hydrodynamic focusing," Lab on a Chip, vol. 9, No. 11 Jan. 1, 2009, p. 1583.
U.S. Appl. No. 13/998,095, filed Apr. 2, 2015, Foster, et al.

\* cited by examiner

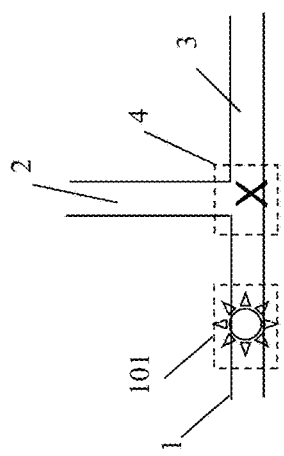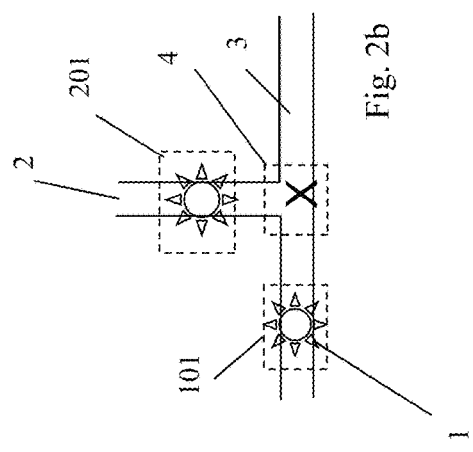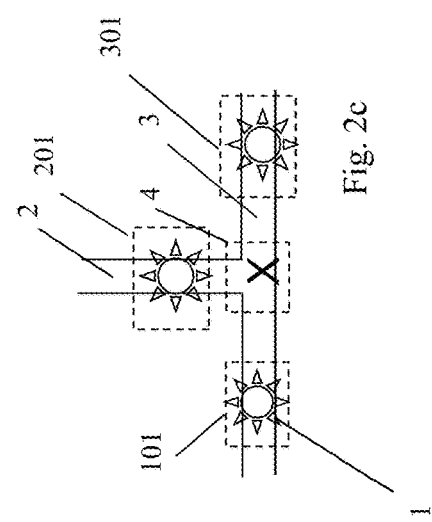

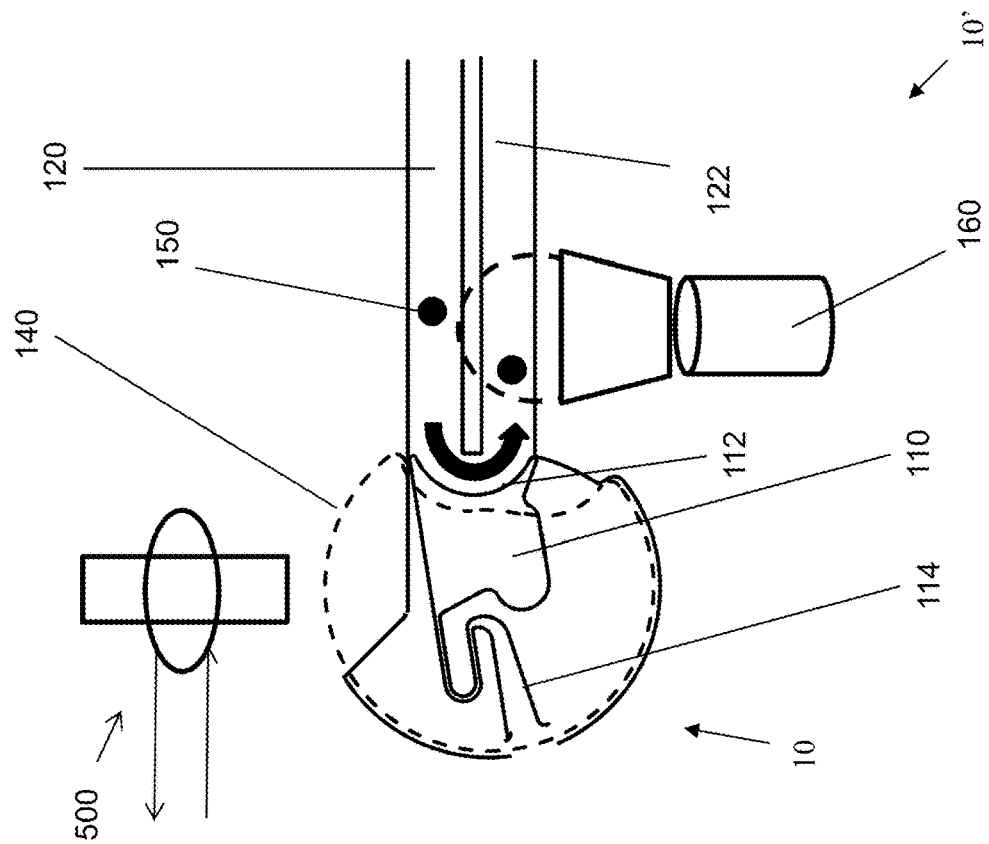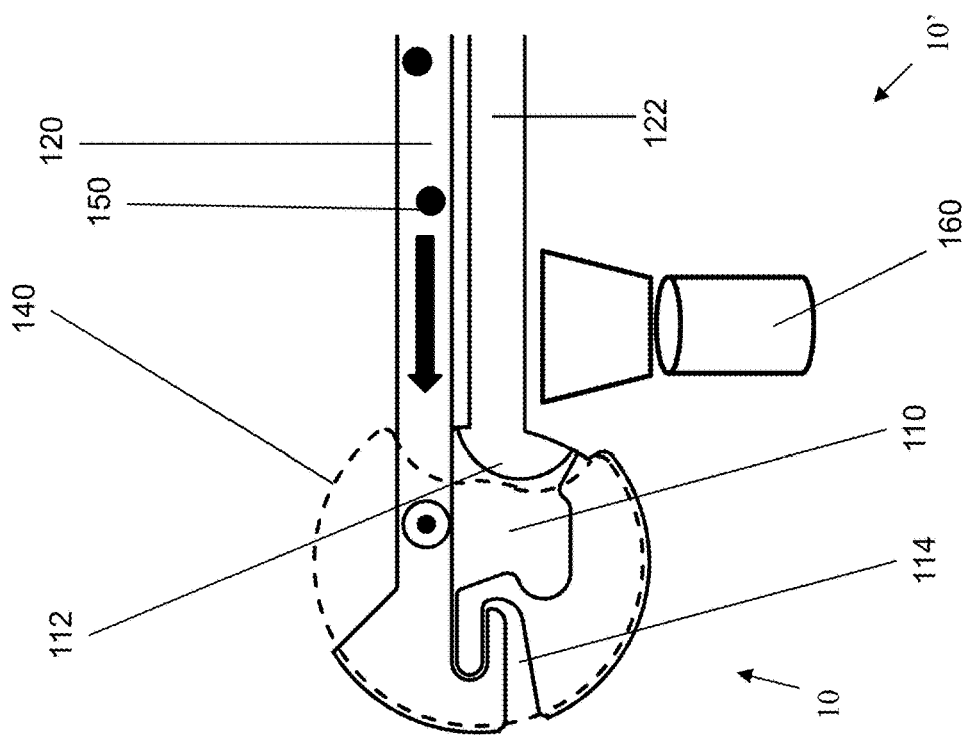

PARTICLE MANIPULATION SYSTEM WITH CAMERA CONFIRMATION

CROSS REFERENCE TO RELATED APPLICATIONS

This US Patent Applications is a continuation-in-part from U.S. patent application Ser. No. 14/947,947, filed Nov. 20, 2015. U.S. patent application Ser. No. 14/947,947 is a divisional based on U.S. patent application Ser. No. 13/507,830, filed Aug. 1, 2012, now U.S. Pat. No. 9,194,786, issued Nov. 24, 2015. Each of these documents is incorporated by reference in their entireties.

STATEMENT REGARDING FEDERALLY SPONSORED RESEARCH

Not applicable.

STATEMENT REGARDING MICROFICHE APPENDIX

Not applicable.

BACKGROUND

This invention relates to a system and method for manipulating small particles in a microfabricated fluid channel.

Microelectromechanical systems (MEMS) are very small, often moveable structures made on a substrate using surface or bulk lithographic processing techniques, such as those used to manufacture semiconductor devices. MEMS devices may be moveable actuators, sensors, valves, pistons, or switches, for example, with characteristic dimensions of a few microns to hundreds of microns. A moveable MEMS switch, for example, may be used to connect one or more input terminals to one or more output terminals, all microfabricated on a substrate. The actuation means for the moveable switch may be thermal, piezoelectric, electrostatic, or magnetic, for example. MEMS devices may be fabricated on a semiconductor substrate which may manipulate particle passing by the MEMS device in a fluid stream.

For example, MEMS devices such as a movable valve, may be used as a sorting mechanism for sorting various particles from a fluid stream, such as cells from blood. The particles may be transported to the sorting device within the fluid stream enclosed in a microchannel, which flows under pressure. Upon reaching the MEMS sorting device, the sorting device directs the particles of interest such as a blood stem cell, to a separate receptacle, and directs the remainder of the fluid stream to a waste receptacle.

MEMS-based cell sorter systems may have substantial advantages over existing fluorescence-activated cell sorting systems (FACS) known as flow cytometers. Flow cytometers are generally large and expensive systems which sort cells based on a fluorescence signal from a tag affixed to the cell of interest. The cells are diluted and suspended in a sheath fluid, and then separated into individual droplets via rapid decompression through a nozzle. After ejection from a nozzle, the droplets are separated into different bins electrostatically, based on the fluorescence signal from the tag. Among the issues with these systems are cell damage or loss of functionality due to the decompression, difficult and costly sterilization procedures between sample, inability to sort sub-populations along different parameters, and substantial training necessary to own, operate and maintain these large, expensive pieces of equipment. For at least these reasons, use of flow cytometers has been restricted to large hospitals and laboratories and the technology has not been accessible to smaller entities.

A number of patents have been granted which are directed to such MEMS-based particle sorting devices. For example, U.S. Pat. No. 6,838,056 is directed to a MEMS-based cell sorting device, U.S. Pat. No. 7,264,972 b1 is directed to a micromechanical actuator for a MEMS-based cell sorting device. U.S. Pat. No. 7,220,594 is directed to optical structures fabricated with a MEMS cell sorting apparatus, and U.S. Pat. No. 7,229,838 is directed to an actuation mechanism for operating a MEMS-based particle sorting system. Additionally, U.S. patent application Ser. Nos. 13/374,899 and 13/374,898 provide further details of other MEMS designs. Each of these patents and patent application publications is hereby incorporated by reference, and each is assigned to Innovative Micro Technology and Owl biomedical, the assignee of the present invention.

SUMMARY

One feature of the MEMS-based particle sorting system is that the fluid may be confined to small, microfabricated channels formed in a semiconductor substrate throughout the sorting process. The MEMS device may be a valve which separates a target particle from other components of a sample stream. The MEMS device may redirect the particle flow from one channel into another channel, when a signal indicates that a target particle is present. This signal may be a photon from a fluorescent tag which is affixed to the target particle and excited by laser illumination in an interrogation region upstream of the MEMS device. Thus, the MEMS device may be a particle or cell sorter operating on a fluid sample.

More generally however, particles in the fluid stream may be manipulated rather than sorted, by some manipulation including heating, tagging, charging, altering or destroying a target particle flowing in a fluid stream. In this scenario, the target particle may be distinguished from the non-target particle by a fluorescence activated detection, such as that used in the above-described FACS flow cytometers. The identified cells may then be manipulated by the particle manipulation stage. This manipulation may be accomplished by a microfabricated device manufactured on a substrate which heats, tags, charges, alters or destroys the target particles. The fabrication substrate may also include microfabricated channels leading to and from the particle manipulation stage.

A system and method are described which makes use of this architecture which is particular to the particle manipulation systems such as those disclosed in the aforementioned patents. These techniques may form a particle manipulation system with cytometric capability, as described below. A microfabricated device may be used to manipulate the particles in the fluid stream enclosed in the microfabricated channel. In this system and method, a plurality of interrogation regions exist within the microfluidic pathways, with one laser interrogation region upstream of the MEMS device, and at least one additional optical interrogation region downstream of the MEMS device. The additional optical interrogation regions may be used to confirm the performance of the microfabricated manipulation device.

The particle manipulation system with cytometric capability may include at least one laser whose radiation is directed into a first laser interrogation region in first portion of a microchannel formed in a substrate, at least one particle manipulation stage formed in the substrate, and cytometric confirmation provided by an optical camera. It should be understood that the term "optical camera" is used to refer to a device which generates a two dimensional rendering of an image in a horizontal and vertical plane. The optical camera typically gathers light through a lens, although a lens may not necessarily be present. The camera generates a two-dimensional image of a scene from the gathered light.

Accordingly, the particle manipulation system may include a particle manipulation stage and a sample stream in a microfluidic inlet channel, an optical interrogation device upstream of the particle manipulation stage which identifies target particles, and an optical confirmation device downstream of the particle manipulation stage, wherein the optical confirmation device uses a camera to determine the presence or absence of a target particle.

In one embodiment, the MEMS device is a microfabricated cell sorter, which sorts a target cell (cancer cell, sperm cell, stem cell for example) from the other components of a fluid stream. The MEMS sorter may be electromagnetically actuated, with a flap or valve which is pulled down into the channel to redirect the flow in response to the detection of a target particle in the channel. This valve may direct the flow into a sort channel rather than the waste channel.

In one embodiment, the camera confirmation may be disposed in the sort channel, where the target particles are directed by the MEMS sorter. By imaging the sorted particles and determining their positional locus, various sort parameters such as gate timing and duration, may be optimized. This optimization may be automatic, under computer control, such that the system may be "self-aware".

These and other features and advantages are described in, or are apparent from, the following detailed description.

BRIEF DESCRIPTION OF THE DRAWINGS

Various exemplary details are described with reference to the following figures, wherein:

FIG. 2a is a simplified illustration of a microfabricated particle manipulation system having an intersection;

FIG. 2b is a simplified illustration of a microfabricated particle manipulation system having an intersection according to one embodiment of the present invention;

FIG. 2c is a simplified illustration of a microfabricated particle manipulation system having an intersection according to another embodiment of the present invention;

FIG. 7a is a simplified plan view of a microfabricated particle sorting system showing the field of view of the detector, with the microfluidic valve in the quiescent (no sort) position; FIG. 7b is a simplified illustration of a microfabricated particle sorting system showing the field of view of the detector, with the microfluidic valve in the actuated (sort) position;

It should be understood that the drawings are not necessarily to scale, and that like numbers maybe may refer to like features.

DETAILED DESCRIPTION

The system described herein is a particle sorting system which may make use of microchannel architecture of a particle manipulation system, such as those disclosed in the aforementioned patents. More generally, the systems and methods describe a particle manipulation system with multiple laser interrogation regions, which form a particle manipulation system with cytometric capability. The multiple laser interrogation regions may provide information as to the effectiveness or accuracy of the particle manipulations, allowing the manipulations to be adjusted or controlled during the process.

In the figures discussed below, similar reference numbers are intended to refer to similar structures, and the structures are illustrated at various levels of detail to give a clear view of the important features of this novel device.

Figure 1A:
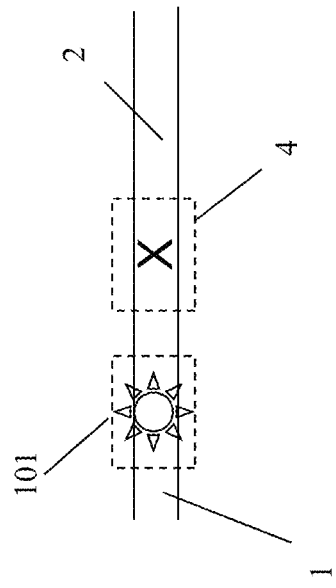
FIG. 1a is a simplified illustration of a microfabricated particle manipulation system.

FIG. 1a is a schematic illustration of a MEMS-based particle manipulation system using lithographically formed microfluidic channels. One microfluidic channel 1 may be an input channel which directs a fluid flow. The fluid stream in microfluidic channel 1 flows through a first laser interrogation region 101. In this region, light from one or more lasers is directed. The light may be focused to a spot and onto the particles flowing in the stream, wherein the laser interrogation region 101 is disposed upstream of a microfabricated manipulation stage 4. If the particles have the appropriate fluorescent tag affixed thereto, the tag may be excited and emit a characteristic fluorescent photon. This photon may be detected by optical detectors and evaluated by appropriate logic circuits. The logic circuits may control the manipulation stage 4, which may manipulate the tagged particles under the control of the logic circuits.

In one exemplary embodiment, the MEMS device may apply a charge to the target particle. In another exemplary embodiment discussed further below, the manipulation stage 4 may be an actuator, which diverts the target particle into a different flow path as the non-target particles.

Figure 1B:
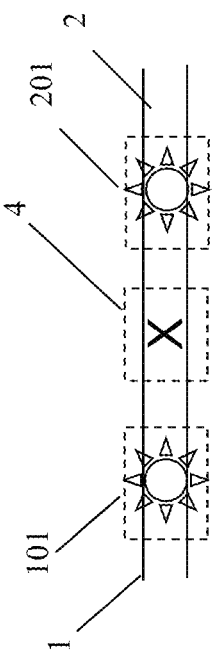
FIG. 1b is a simplified illustration of a microfabricated particle manipulation system according to the present invention.

FIG. 1b is a schematic illustration of a particle manipulation system with cytometric capability 10, which uses lithographically formed microfluidic channels, according to the present invention. One microfluidic channel 1 may be an input channel which directs a fluid flow into a manipulation stage 4. Microfabricated device 4 may alter the trajectory, morphology, shape, charge or other characteristic of the particle. Another microfluidic channel 2 directs the fluid flow away from the manipulation stage 4 and into an output channel. A second laser interrogation region 201 may be positioned in microfluidic channel 2. Using laser interrogation region 201 to interrogate the passing particles, the effectiveness, accuracy and/or efficiency of MEMS manipulation stage 4 can be assessed. The simultaneous detection of fluorescence and the manipulated characteristic indicates accurate performance of the manipulation stage.

For example, manipulation stage 4 may apply a charge to a passing particle. Laser interrogation stage 2 may confirm the presence of both the charge and the fluorescent tag by measuring the voltage on a parallel plate capacitor (not shown) installed in the channel 2. By so doing, the coincidence of both the fluorescence and the voltage signal is evidence that the charge is correctly place on tagged particles. In the case of a particle or cell sorter, the presence of the target sorted particle in the sort passage where the additional laser interrogation stage 201 is placed, may indicate correct and effective sorting.

FIG. 2a is a schematic illustration of another particle manipulation system with cytometric capability, using lithographically formed microfluidic channels. In FIG. 2a, two or more channels are formed at the output of the manipulation stage 4, forming an intersection point. One channel 2 may move in one path away from the manipulation stage 4, whereas another channel 3 may move in another path away from manipulation stage 4. FIG. 2b depicts a particle manipulation system with cytometric capability. As shown in FIG. 2b, channel 2 may be equipped with an additional laser interrogation stage 201, which may identify the various particles according to their response to irradiation with laser light. If a particle emits a photon in response to irradiation, that is an indication that it is a tagged, target particle. If it does not, it is likely an untagged, non-target particle.

As shown in FIG. 2c, both channels 2 and 3 may be equipped with an additional laser interrogation stage 201 and laser interrogation stage 301, which may identify the various particles according to their response to irradiation with laser light. Indeed, any number of additional laser interrogation regions may be placed in any number of microfluidic channels, although large numbers of such regions may become difficult to separate, as described more fully below. As before, if a particle emits a photon in response to irradiation, that is an indication that it is a tagged, target particle. If it does not, it is likely an untagged, non-target particle. These two laser interrogation stages may measure the difference in density of target particles in one channel 2 relative to the other channel 3 or input channel 1.

Figure 3A:
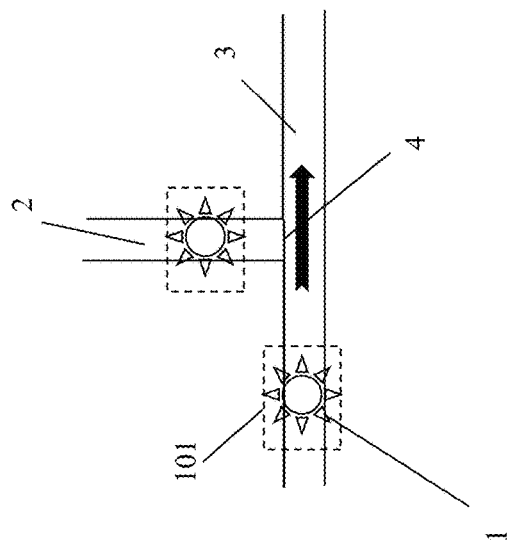
FIG. 3a is a simplified illustration of a microfabricated particle sorting system according to one embodiment of the present invention, with the sort valve in the closed position.

FIG. 3a is a schematic illustration of a particle manipulation system with cytometric capability 10 using multiple laser interrogation regions disposed in lithographically formed microfluidic channels. The manipulation stage 4 may be a MEMS flap-type actuator or sorter. The MEMS flap-type actuator is shown only schematically in FIG. 5, and may be a flap-type fluidic valve which separates a target particle from a remainder of the sample stream, based on a signal from the first laser interrogation region. The MEMS flap-like actuator may be a simple, hinge mounted movable member that may be drawn downward in response to a force acting on the movable member. The force may be, for example, electrostatic, magnetostatic or electromagnetic. The movable member may be formed lithographically on a silicon substrate, and methods for manufacturing such a device may be found in the above-incorporated patents and patent applications.

The MEMS actuator may divert the incoming fluid stream into one of the plurality of exit channels, for example into either channel 2 or channel 3. For example, if a signal from laser interrogation region 101 indicates that a target particle is present, the logic circuit coupled to laser interrogation region 101 may send a signal to the MEMS actuator 4 to activate the flap. Drawing down the flap will divert the detected target particle into the sort channel 2 rather than allowing it to flow past into waste channel 3.

Figure 3B:
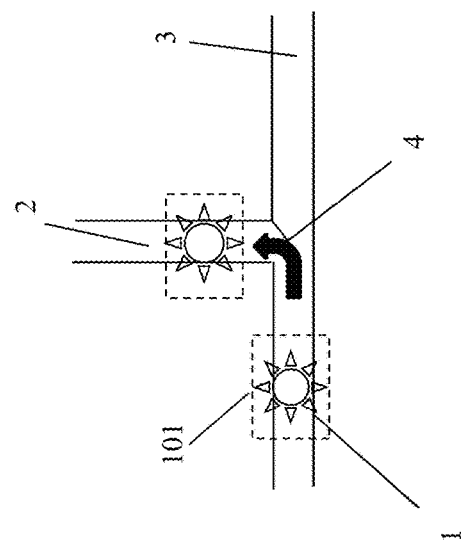
FIG. 3b is a simplified illustration of a microfabricated particle sorting system according to one embodiment of the present invention, with the sort valve in the open position.
Figure 4A:
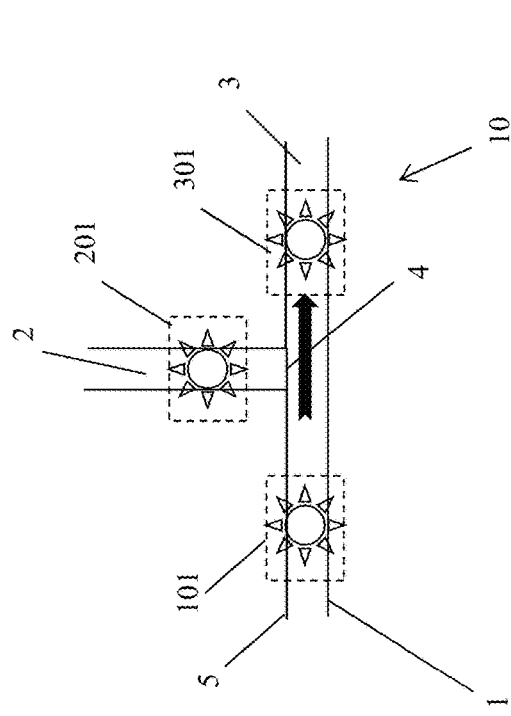
FIG. 4a is a simplified illustration of a microfabricated particle sorting system according to another embodiment of the present invention, with the sort valve in the closed position.
Figure 4B:
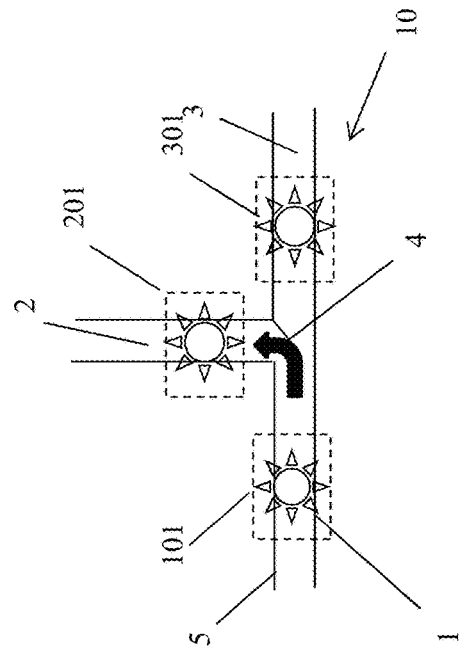
FIG. 4b is a simplified illustration of a microfabricated particle sorting system according to another embodiment of the present invention, with the sort valve in the open position.

As mentioned previously, waste channel 3 may also be equipped with an additional laser interrogation region 301. This arrangement is shown in FIGS. 4a and 4b, which are similar to FIGS. 3a and 3b, except that two laser interrogation regions 201 and 301 are disposed in sort channel 2 and waste channel 3, respectively. The two additional interrogation regions 201 and 301 may measure the increased density of target cells in sort channel 2 compared to waste channel 3, and thus may provide evidence of the effectiveness and accuracy of the MEMS sorter 4 and laser interrogation region 101.

Thus, as can be seen from the figures above, the additional laser interrogation regions 201 and 301 (or more) may act as a cytometer or as a quality control measure. The system 10 may give feedback as to the correct setting of any adjustable parameters in the sorting algorithm. Such parameters may include, for example, fluorescent pulse shape, width, magnitude or duration, laser intensity, optical alignment or focusing. These parameters may then be adjusted during the sort, rather than waiting for the entire sample to be processed before finding a problem in the sorting. The presence of additional laser interrogation regions 201 and/or 301 may provide cytometer capability to the sorter, in that it is able to count, enumerate, or quantify the density or purity of the sorted sample, while the sorting process is underway. This capability may allow the sort process to be adjusted in real time, that is, while it is underway. This may allow an optimization of sort parameters without performing multiple sorting operations on a sample, thus saving time and sample volume.

Figure 5:
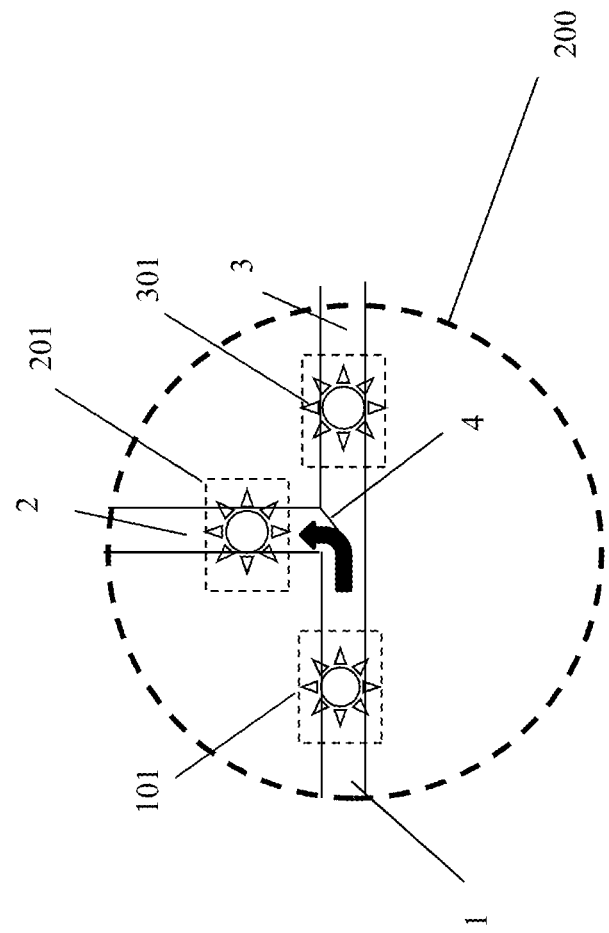
FIG. 5 is a simplified illustration of a microfabricated particle sorting system according to an embodiment of the present invention, showing the field of view of the detector compared to the interrogation regions.

Also shown in FIG. 5 is the field of view 200 of the detector monitoring laser interrogation region 101 as well as additional laser interrogation regions 201 and 301. As indicated in FIG. 5, all laser interrogation regions may fall within the detector field of view, and thus may share at least a portion of the optical and electronic data detection channel. Accordingly, light collected from the at least one additional laser interrogation region is collected by an optical system which also collects light from the first laser interrogation region. Details as to how to exploit or implement this feature are set forth below with respect to the remaining figures.

Figure 6:
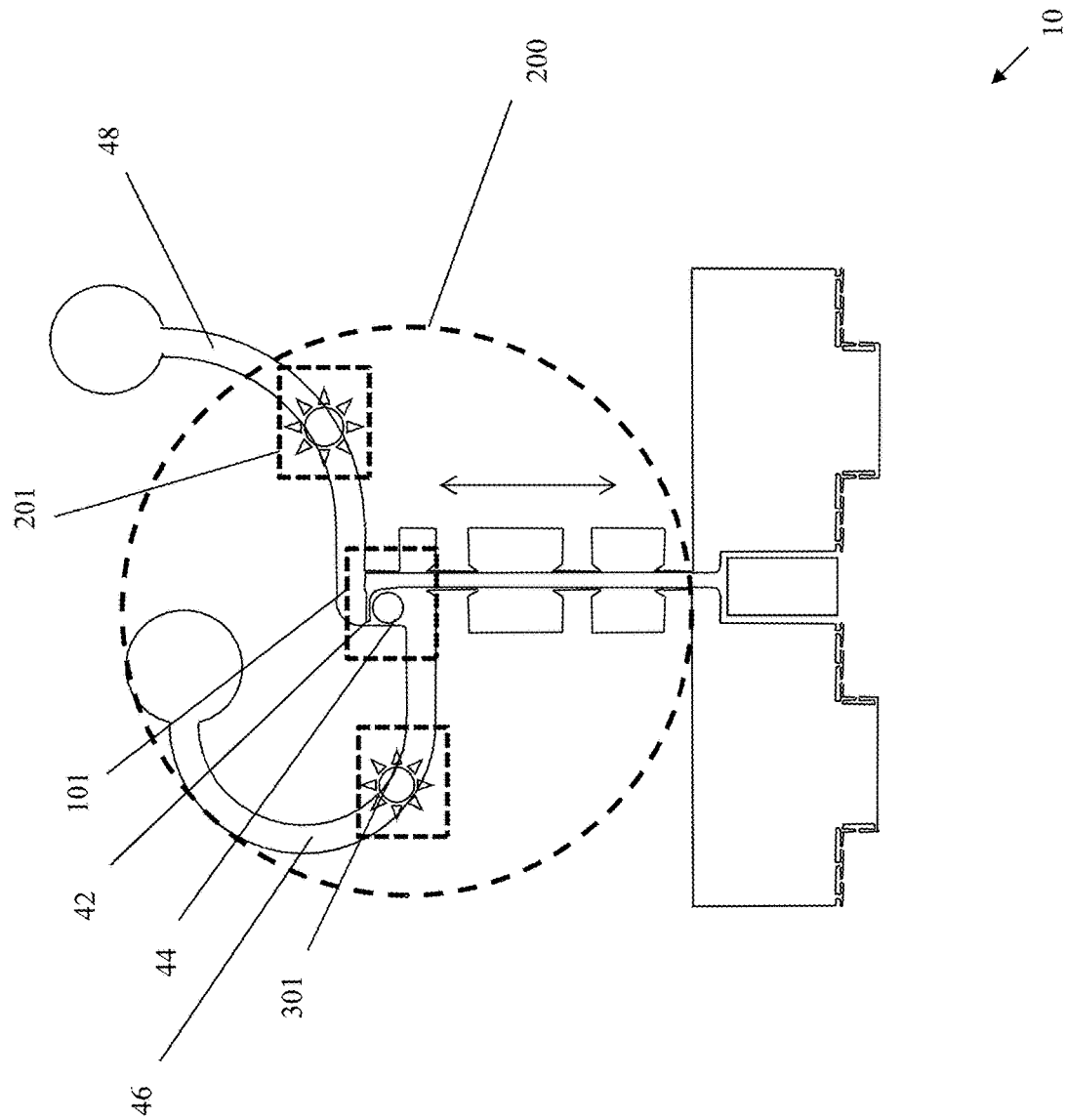
FIG. 6 is a simplified illustration showing further detail of one embodiment of a microfabricated particle sorting system according to the present invention.

FIG. 6 shows another exemplary embodiment of a particle manipulation system with cytometric capability 40. FIG. 6 shows details of an actual implementation of the plurality of laser interrogation regions on a MEMS actuator in a particle manipulation system 40. In this diagram, a sort channel 48 flows upward from the diverter and the waste channel 46 flows downward, and the diverter is positioned at the bottom of a vertical channel 44 (perpendicular to the paper). This actuator may use a magnetically actuated diverter 42, to shift the fluid flow exiting a vertical channel 44 from the lower, waste channel 46 to the upper, sort channel 48. The diverter may be actuated in response to a fluorescent signal emanating from a target cell which has been tagged with a fluorescent marker. This "fluorescence activated cell sorting" (FACS) technique is similar to the detection methodologies used in flow cytometers. The detection occurs in the first laser interrogation region 101 disposed in the vertical channel 44 as shown in FIG. 6. The success or failure of the sorting can be confirmed by disposing an additional laser interrogation region 201 and/or 301 in either or both of the sort channel 48 and waste channel 46, respectively. Additional details relating to the design and manufacture of the microfabricated electromagnetic diverter may be found in the incorporated patents.

As shown in FIGS. 5 and 6, the approximate field of view of the detection optics may cover all laser interrogation regions 101, 201 and 301, as described in greater detail below. Of note in FIGS. 5 and 6, since the field of view of the detection optics is sufficiently large to include laser interrogation region 101, as well as laser interrogation region 201, and even laser interrogation region 301, or more, the multiple laser interrogation regions may share at least a portion of an optical detection path. This is a result of the small scale of the microfabricated cell sorter and associated microfluidic channels. Each of the channels 1, 2 and 3 may be on the order of 20 microns in width. The distance between laser interrogation region 1 and MEMS cell sorter 4 may be kept below 500 microns or so, in order to reduce the timing uncertainty between the passage of the target particle and the opening of the MEMS cell sorting valve 4. As this distance gets longer, the additional uncertainty may mean that a non-target particle is allowed into the sort channel 2, or a target particle is allowed to pass into waste channel 3. Either of these events reduces the purity or the yield of the sorted sample. Accordingly, to optimize the sort performance, the distance between the detection region and the sorter may be kept as short as practical.

While the particle manipulation in this embodiment is a cell sorter, it should be understood that any number of particle manipulations may be performed, such as tagging, charging, heating, altering and destroying rather than sorting.

In general, the valves, actuators or manipulators 4 used herein may be formed on a semiconductor substrate using lithographic techniques well known in MEMS fabrication. Details of their fabrication techniques may be found in the aforementioned patents. Thus, a characteristic dimension, for example its total width or length of the structure may be about 500 microns or less, and the fluidic channels may be formed in the same substrate with characteristic dimensions of about 10-20 microns.

FIG. 7a is a plan view illustration of another embodiment of a novel microfabricated fluidic device 10' in the quiescent (un-actuated) position. The device 10' may include a microfabricated fluidic valve or movable member 110 and a number of microfabricated fluidic channels 120, 122 and 140. The fluidic valve 110 and microfabricated fluidic channels 120, 122 and 140 may be formed in a suitable substrate, such as a silicon substrate, using MEMS lithographic fabrication techniques as described in greater detail below. The fabrication substrate may have a fabrication plane in which the device is formed and in which the movable member 110 moves. The movable member 110 may comprise at least a portion of this substrate material.

A sample stream may be introduced to the microfabricated fluidic valve 110 by a sample inlet channel 120. The sample stream may contain a mixture of particles, including at least one desired, target particle 150 and a number of other undesired, non-target material. The particles may be suspended in a fluid. For example, the target particle 150 may be a biological material such as a stem cell, a cancer cell, a zygote, a protein, a T-cell, a bacteria, a component of blood, a DNA fragment, for example, suspended in a buffer fluid such as saline. The inlet channel 120 may be formed in the same fabrication plane as the valve 110, such that the flow of the fluid is substantially in that plane. The motion of the valve 110 may also be within this fabrication plane.

The decision to sort/save or dispose/waste a given particle may be based on any number of distinguishing signals. In one exemplary embodiment, the decision is based on a fluorescence signal emitted by the particle, based on a fluorescent tag affixed to the particle and excited by an illuminating laser. Details as to this detection mechanism are well known in the literature, and further discussed below with respect to FIG. 14. However, other sorts of distinguishing signals may be used, including scattered light or side scattered light which may be based on the morphology of a particle, or any number of mechanical, chemical, electric or magnetic effects that can identify a particle as being either a target particle, and thus sorted or saved, or an nontarget particle and thus rejected or otherwise disposed of.

With the valve 110 in the position shown, the input stream passes unimpeded to an output orifice and channel 140, which is out of the plane of the inlet channel 120, and thus out of the fabrication plane of the device 10'. That is, the flow is from the inlet channel 120 to the output orifice 140, from which it flows substantially vertically, and thus substantially orthogonally to the inlet channel 120. This output orifice 140 leads to an out-of-plane channel that may be substantially perpendicular to the plane of the paper as shown in FIG. 7a. More generally, the output channel 140 is not parallel to the plane of the inlet channel 120 or sort channel 122, or the fabrication plane of the movable member 110.

A relieved area above and below the sorting valve or movable member 110 may allow fluid to flow above and below the movable member 110 to output orifice 140. Further, the movable member 110 may have a curved diverting surface 112 which can redirect the flow of the input stream into a sort output stream. The contour of the orifice 140 may be such that it overlaps some, but not all, of the inlet channel 120 and sort channel 122. By having the contour 140 overlap the inlet channel, and with relieved areas described above, a route exists for the input stream to flow directly into the waste orifice 140 when the movable member or valve 110 is in the un-actuated waste position.

FIG. 7b is a plan view of the microfabricated device 10' in the actuated position. In this position, the movable member or valve 110 is deflected upward into the position shown in FIG. 7b. The diverting surface 112 is a sorting contour which redirects the flow of the inlet channel 120 into the sort output channel 122. The arrow in FIG. 7b shows the path of a sorted particle 150. The sort output channel 122 may lie in substantially the same plane as the inlet channel 120, such that the flow within the sort channel 122 is also in substantially the same plane as the flow within the inlet channel 120. There may be an angle α between the inlet channel 120 and the sort channel 122, This angle may be any value up to about 90 degrees. Actuation of movable member 110 may arise from a force from force-generating apparatus 500, shown generically in FIG. 7b. In some embodiments, force-generating apparatus may be an electromagnet, however, it should be understood that force-generating apparatus may also be electrostatic, piezoelectric, or some other means to exert a force on movable member 110, causing it to move from a first position (FIG. 7a) to a second position (FIG. 7b).

Electromagnet 500 may include a current-carrying coil wrapped around a ferromagnetic core, which produces a magnetic field when the coil is energized. This field may attract an inlaid permeable material disposed in the movable member 110. The structure and its formation are discussed more fully in U.S. Pat. No. 9,372,144 issued Jun. 21, 2016 and assigned to the same assignee as the present application. This patent is incorporated by reference in its entirety.

The micromechanical particle manipulation device 10 or 10' may include a microfabricated, movable member 110 having a first diverting surface 112, wherein the movable member 110 moves from a first position to a second position in response to a force applied to the movable member, wherein the motion is substantially in a plane parallel to the surface, a sample inlet channel 120 formed in the substrate and through which a fluid flows, the fluid including one or more target particles and non-target material, wherein the flow in the sample inlet channel is substantially parallel to the surface, and a plurality of output channels 122, 140 into which the microfabricated member diverts the fluid. The flow in at least one of the output channels 140 is not parallel to the plane, and wherein at least one output channel 140 is located directly below at least a portion of the movable member 110 over at least a portion of its motion. Among the plurality of output channels may be a sort output channel into which the microfabricated member diverts the target particles. There may also be a waste output channel into which the non-target material flows, and wherein the flow in waste output channel is substantially orthogonal to the plane, and wherein the waste output channel is located directly below at least a portion of the microfabricated member over at least a portion of its motion.

Because the movable member 110 is formed in and from a single substrate, portions of the movable member 110, especially including the hinge area 114, may comprise the material of the substrate. If a single crystal silicon substrate is used, for example, the hinge or spring 114 may be made of single crystal silicon, which may have advantageous properties.

In one embodiment, the diverting surface 112 may be nearly tangent to the input flow direction as well as the sort output flow direction, and the slope may vary smoothly between these tangent lines. In this embodiment, the moving mass of the stream has a momentum which is smoothly shifted from the input direction to the output direction, and thus if the target particles are biological cells, a minimum of force is delivered to the particles. As shown in FIGS. 7a and 7b, the micromechanical particle manipulation device 10' has a first diverting surface 112 with a smoothly curved shape, wherein the surface which is substantially tangent to the direction of flow in the sample inlet channel at one point on the shape and substantially tangent to the direction of flow of a first output channel at a second point on the shape, wherein the first diverting surface diverts flow from the sample inlet channel into the first output channel when the movable member 110 is in the first position, and allows the flow into a second output channel in the second position.

In other embodiments, the overall shape of the diverting surface 112 may be circular, triangular, trapezoidal, parabolic, or v-shaped for example, but the diverter serves in all cases to direct the flow from the inlet channel to another channel.

It should be understood that although channel 122 is referred to as the "sort channel" and orifice 140 is referred to as the "waste orifice", these terms can be interchanged such that the sort stream is directed into the waste orifice 140 and the waste stream is directed into channel 122, without any loss of generality. Similarly, the "inlet channel" 120 and "sort channel" 122 may be reversed. The terms used to designate the three channels are arbitrary, but the inlet stream may be diverted by the valve 110 into either of two different directions, at least one of which does not lie in the same plane as the other two. The term "substantially" when used in reference to an angular direction, i.e. substantially tangent or substantially vertical, should be understood to mean within 15 degrees of the referenced direction. For example, "substantially orthogonal" to a line should be understood to mean from about 75 degrees to about 105 degrees from the line.

FIGS. 7a and 7b illustrate an embodiment wherein the angle α between the inlet channel 120 and the sort channel 122 is approximately zero degrees. Accordingly, the sort channel 122 is essentially antiparallel to the inlet channel 120, such that the flow is from right to left in the inlet channel 120, and left to right in the sort channel 122. With valve 110 in the un-actuated, quiescent position shown in FIG. 7a, the inlet stream may flow straight to the waste orifice 140 and vertically out of the device 10'. With the movable member 110 actuated a shown in FIG. 7b, the flow in the sort channel 122 in substantially antiparallel to the flow in input channel 120.

Although the embodiments shown in FIGS. 1-7 are described with respect to an electromagnetic actuation mechanism, it should be understood that other actuation forces may be used instead. For example, if permeable features are made from an electrically conductive rather than permeable magnetic material, a voltage potential may be placed across elements, producing an electrostatic force to move the movable member 110. Piezoelectric forces may also be used.

Figure 8:
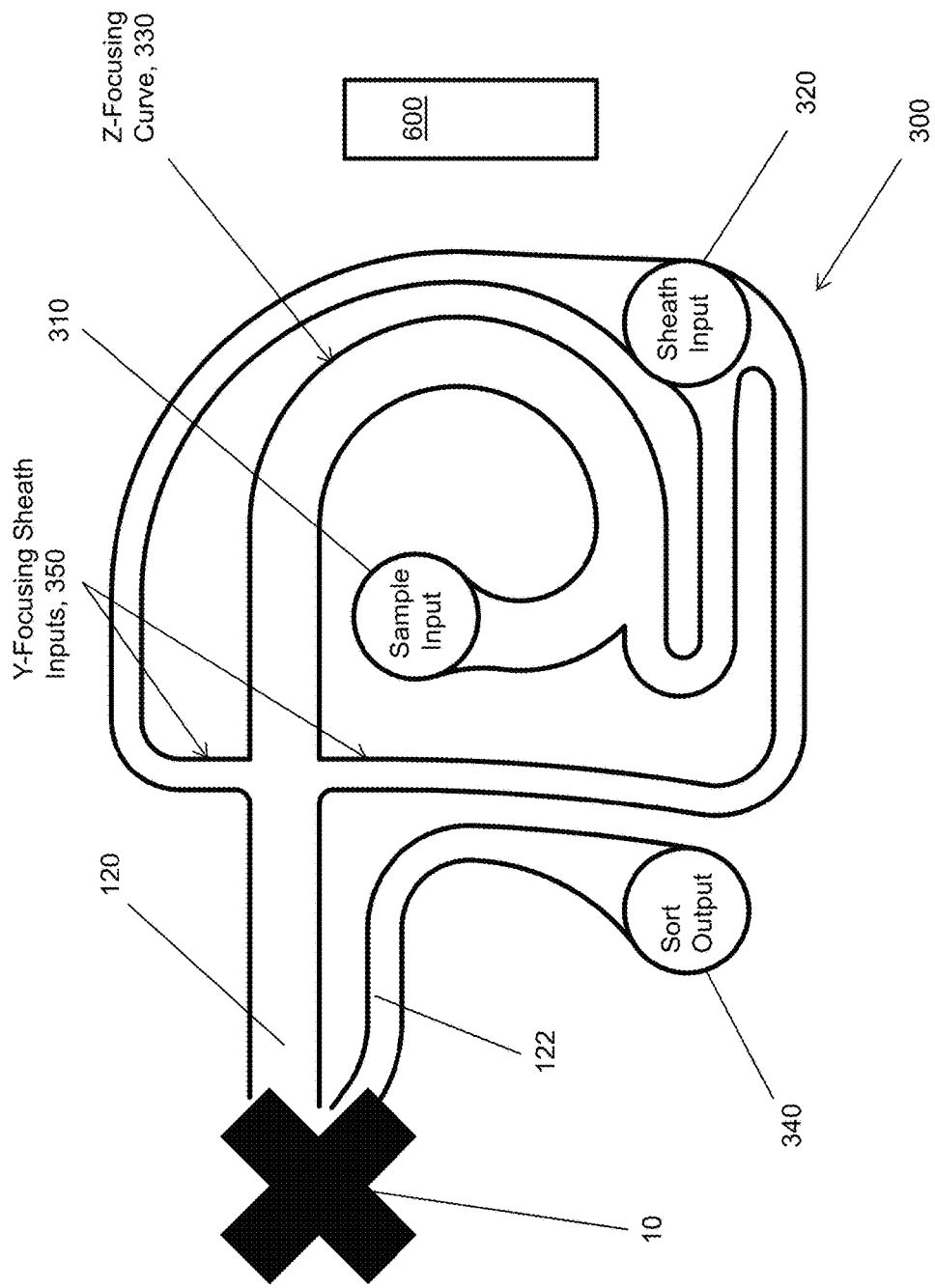
FIG. 8 is a plan view of the microfabricated particle sorting system in combination with a hydrodynamic focusing manifold.

Because of the microfabricated architectures of particle manipulation devices 10 and 10', they may lend themselves to techniques that can make use of such an enclosed, well defined microfluidic architecture. One such technique is illustrated in FIG. 8, wherein the microfabricated particle manipulation device may have at least one additional channel that provides a sheath fluid to the sample stream and also a focusing element coupled to the inlet channel. The sheath fluid may be used to adjust the concentration or positioning of the target particles 150 within the inlet channel. The focusing element may be configured to urge the target particles into a particular portion of the sample inlet channel, as described further below. The focusing element may be disposed in substantially the same plane as the movable member 110, and may be formed in the same substrate surface as the movable member 110 and inlet channel 120.

FIG. 8 depicts a microfabricated fluidic manifold 300 which may be used to focus the particles in a certain area within the fluid stream. Techniques for designing such a manifold may be found in, for example, "Single-layer planar on-chip flow cytometer using microfluidic drifting based three-dimensional (3D) hydrodynamic focusing," by Xiaole Mao et cl, Journal of Royal Society of Chemistry, Lab Chip, 2009, 9, 1583-1589. The manifold may include a sample inlet 310 and sheath fluid channel 320. As the name suggests, the sheath channel adds a sheath fluid to the sample stream, which is a buffering fluid which tends to dilute the flow of particles in the stream and locate them in a particular portion of the stream. The combined fluid then flows around a focusing element coupled to the inlet channel 120, here a z-focusing channel 330, which tends to herd the particles into a particular plane within the flow. This plane is substantially in the plane of the paper of FIG. 8. The combined fluid then passes another intersection point, a "y-intersection point" 350, which introduces additional sheath fluid above and below the plane of particles. At the y-intersection point 350, two flows may join the z-focus channel 330 from substantially antiparallel directions, and orthogonal to the z-focus channel 330. This intersection may compress the plane of particles into a single point, substantially in the center of the stream. Accordingly, at the y-intersection point 350 the target particles may be compressed from a plane to a stream line near the center of the z-focus channel 330 and sample inlet channel 120. Focusing the particles into a certain volume tends to decrease the uncertainly in their location, and thus the uncertainty in the timing of the opening and closing of the movable member or valve 110. Such hydrodynamic focusing may therefore improve the speed and/or accuracy of the sorting operation.

In one exemplary embodiment of the microfabricated particle manipulation device 10 or 10' with hydrodynamic focusing illustrated in FIG. 8, the angular sweep of z-bend 330 is a curved arc of at least about 180 degrees. That is, the approximate angular sweep between the junction of the sheath inlet with the sample inlet and the y-intersection point 350, may be at least about 180 degrees. Generally, the radius of curvature of the z-bend 330 may be at least about 100 microns and less than about 500 microns, and the characteristic dimension, that is the width, of the channels is typically about 50 microns to provide the focusing effect. In one embodiment, the radius of curvature of the channel may be about 250 microns, and the channel widths, or characteristic dimensions, for the sample inlet channel 120 and z-bend channel are on the order of about 50 microns. These characteristic dimensions may provide a curvature sufficient to focus the particles, such that they tend to be confined to the plane of the paper upon exit from the z-focus channel 330 at y-intersection point 350. This plane is then compressed to a point in the channel at the y-intersection point 350. Additional details of this focusing architecture may be found in U.S. patent application Ser. No. 13/998,096 filed Oct. 1, 2013 and assigned to the same assignee as the instant application. This '096 application is incorporated by reference in its entirety. These techniques are particularly suited to such low Reynolds number environments like the flows through these very narrow microchannels.

A focusing effect may also be achieved by applying acoustic energy to the microfabricated channels. An acoustic source 600 may be coupled mechanically to a surface of the substrate shown in FIG. 8, in order to deliver acoustic energy to the particles 150 in the sample stream. Because of the differing acoustic properties of the particles with respect to the surrounding fluid, the acoustic energy may tend to concentrate the particles near the center of the flow within the channel.

Accordingly, a particle manipulation stage may include a microfabricated cell sorting device. The microfabricated cell sorting device may move in a plane, and may be disposed in a microfluidic channel through which a sample stream flows, wherein the microfluidic channel is also formed in the plane, and wherein the sample stream includes target particles and non-target material. The particle manipulation system may further comprise a sheath fluid inlet in fluid communication with the microfluidic inlet channel, and a focusing element coupled to the sheath fluid inlet, which is configured to urge the target particles into a particular portion of the microfluidic inlet channel.

The focusing element may comprise a z-focus channel, wherein the z-focus channel curves in an arc of about 180 degree from the sheath fluid inlet, and urges the target particles into substantially a single plane. The z-focus channel may have a radius of curvature of at least about 100 microns and less than about 500 microns. The focusing element may be disposed in the same plane as the microfabricated cell sorting valve, and formed in the same substrate. The inlet channel and z-focus channel may both have characteristic dimensions of about 50 microns. The focusing element may be disposed in the same plane as the microfabricated cell sorting device, and formed in the same substrate. The focusing element may also include an acoustic focusing element, which urges the target particles using sound waves.

The microfabricated devices operating in microfluidic channels suggest that a well-defined region exists downstream of the sorting operation. In this region, a confirmation device can operate in a well-defined region as was discussed above. In one embodiment, a camera can evaluate the results of the sorting operation by detecting the presence and position of the target particles 150 within the field of view of the camera. One such camera-based imaging system is shown as 160 in FIGS. 7a and 7b, and will be described further below.

The system described below is a particle manipulation system which may make use of the microchannel architecture of the MEMS particle sorting devices 10 and 10' and optionally, a focusing element, as described above. The particle manipulation system 100 may make use of a microfabricated MEMS sorting device 10 or 10', and downstream of the sorting device, may include an optical camera (or some other device) 160 to evaluate the result of the manipulation. In this embodiment, the cytometric confirmation is the optical camera which may image the sorted particles 150 in the sample stream.

In the figures discussed below, similar reference numbers are intended to refer to similar structures, and the structures are illustrated at various levels of detail to give a clear view of the important features of this novel device. It should be understood that these drawings do not necessarily depict the structures to scale, and that directional designations such as "top," "bottom," "upper," "lower," "left" and "right" are arbitrary, as the device may be constructed and operated in any particular orientation. In particular, it should be understood that the designations "sort" and "waste" are interchangeable, as they only refer to different populations of particles, and which population is called the "target" or "sort" population is arbitrary.

The particle manipulation system with cytometric confirmation described above, and embodied in FIGS. 1-6 relied on laser interrogation regions 101, 201, and 301 to provide the cytometric confirmation. The systems used at least one additional laser interrogation region downstream of the particle manipulation stage, to evaluate the results of the particle manipulation.

In the systems and methods disclosed from this point forward however, the cytometric confirmation may be provided by an optical camera, rather than a laser interrogator. It should be understood that the term "optical camera" is used to refer to a device which generates a two dimensional rendering of an image in a horizontal and vertical plane. The optical camera typically gathers light through a lens, although a lens may not necessarily be present. The camera generates a two-dimensional image of a scene from the gathered light.

Optical cameras may use a pixelated imaging mechanism, such as a charge coupled device him (CCD) camera or a photomultiplier tube. In one embodiment described here, the optical camera gathers light through an objective lens, and renders a two-dimensional image of the field of view on a display. The display maybe the monitor of a computer screen for example.

Figure 9:
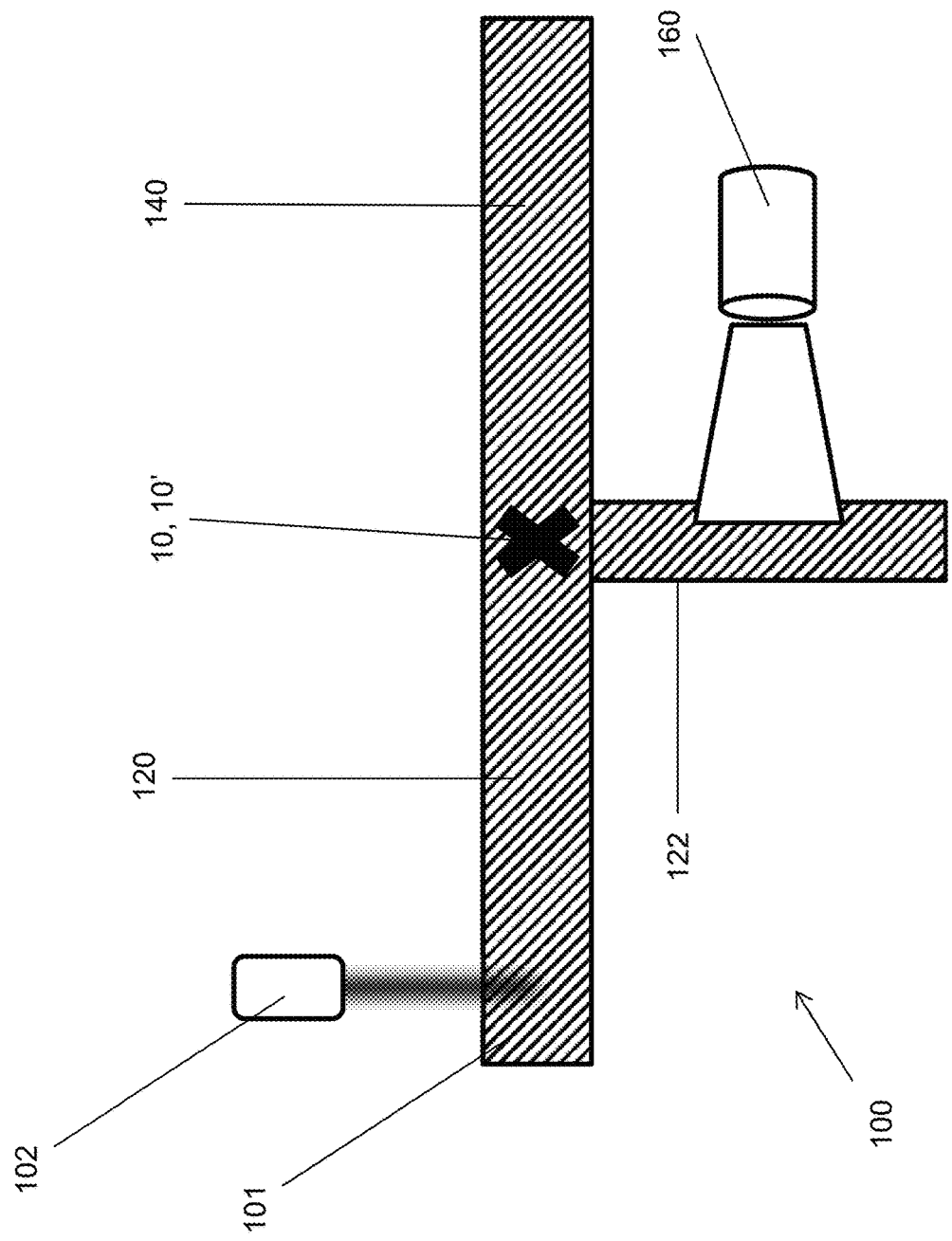
FIG. 9 is a simplified schematic plan view of the microfabricated particle manipulation system with optical camera confirmation.

A simplified plan view of the particle manipulation system with cytometric confirmation using an optical camera 100 is shown in FIG. 9. Shown in FIG. 9 is the input channel 120, the sort channel 122, and the waste channel 140. It should be understood that the waste channel 140 maybe in a different plane than the input channel 120 and sort channel 122, as described above with respect to FIG. 7a, b. However, for ease of the depiction, the waste channel 140 is shown as being in the same plane as the other two channels 120 and 122.

Laser interrogation region 101 is shown in the input channel 120 upstream of the particle manipulation stage 10. The output of a laser 102 may be directed into the laser interrogation region 101 in the input channel 120. A particle manipulation stage 10 or 10' may be disposed at the junction of the input channel 120 with the sort channel 122 and waste channel 140. Particle manipulation stage 10 or 10' may be any of the above described particle sorting mechanisms such as 10 shown in FIG. 6, or 10' shown in FIG. 7a, 7b. The optical camera 160 may be disposed in the sort channel 122 (or optionally in the waste channel) in proximity to the particle manipulation stage 10. The optical camera 160 may have a field of view that includes at least a portion of the sort channel 122 and also may include a portion of the valve mechanism. The optical camera 160 may take an image of the particles in the stream passing through the sort channel 122 through the optically transmissive layer that covers the microfabricated channels 120 and 122 made in the substrate, as described above. The field of view of the camera 160 may include the sorting mechanism, which may be helpful for assessing its condition, as well as measuring the velocity pf the particle through the particle manipulation stage, for example.

Figure 10:
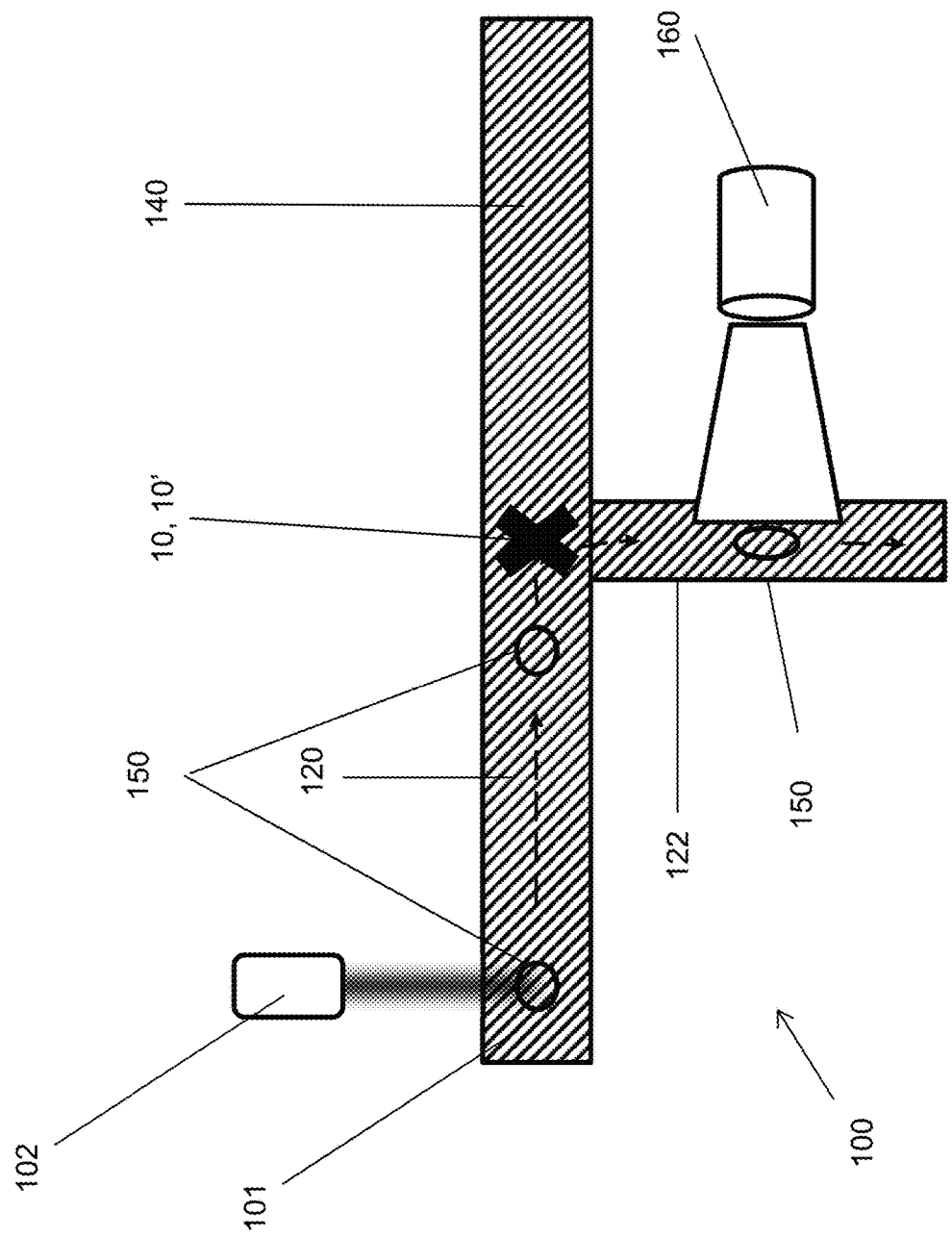
FIG. 10 is a simplified schematic plan view of the microfabricated particle manipulation system with camera confirmation, showing the path of a target particle within the system.
Figure 14:
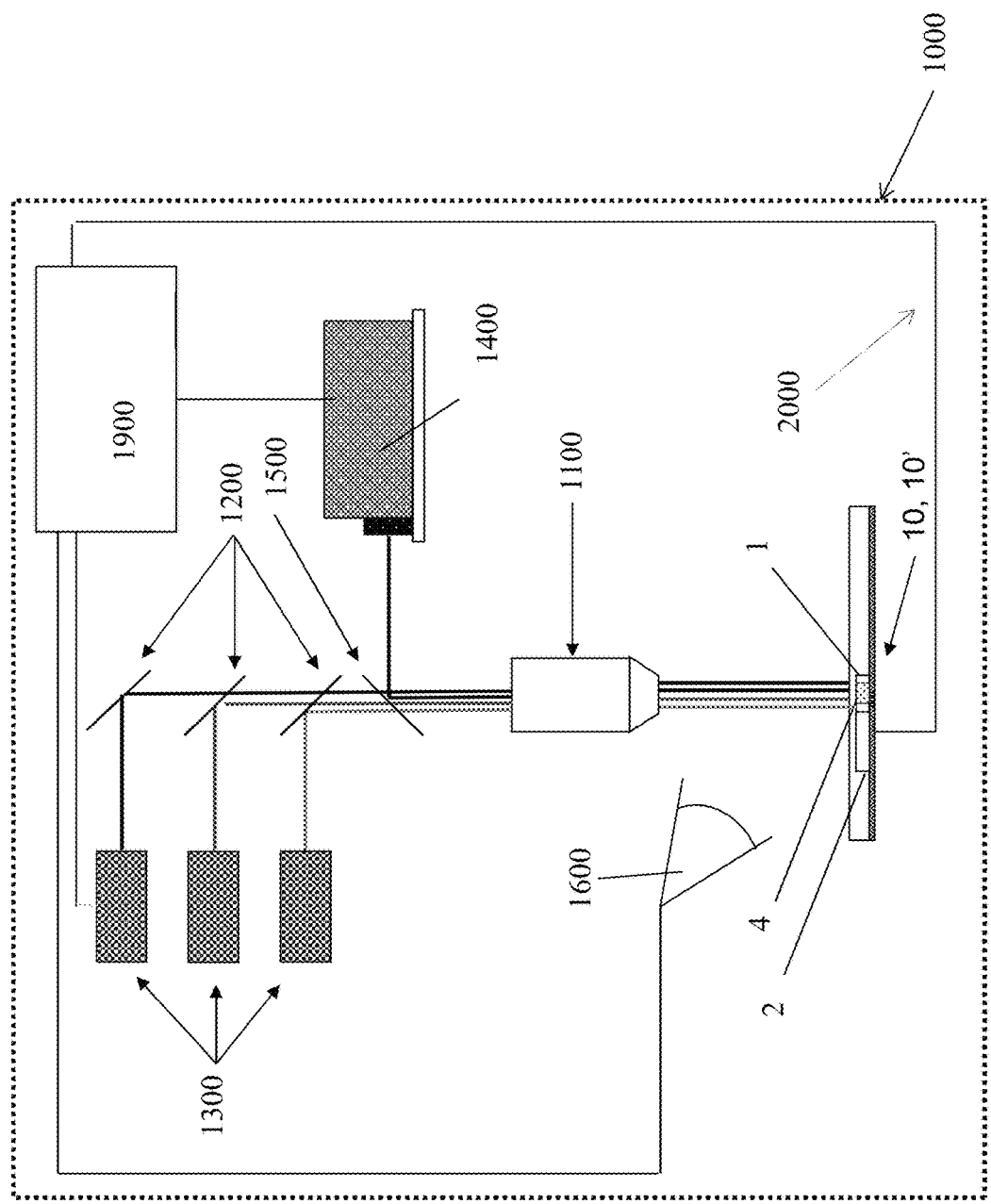
FIG. 14 is a system-level view of the microfabricated particle manipulation system.

FIG. 10 is a schematic view of the particle manipulation system with camera confirmation 100 in operation. In operation, the particle manipulation system with camera confirmation 100 may have one or more target particles 150 flowing in the sample stream in the input channel 120 and through the laser interrogation region 101. The laser will irradiate the target particle 150 which will then fluoresce as a result of the irradiation. The fluorescence will be detected by detector which is not shown in FIG. 10. The output of this detector may be delivered to a controller 1900 (FIG. 14). This controller then may send out a sort trigger pulse which may cause the movable member 110 of the microfabricated particle manipulation stage 10 to move to the sort position as was shown in FIG. 7b.

This sort trigger pulse may also arm optical camera 160, and prepare it to capture an image of the sort channel 122. Accordingly, the optical camera 160 and the particle manipulation stage 10 maybe controlled by the same signal, and based on the detected fluorescence. These control signals may be generated by a controller 1900, which is shown in the system level view of FIG. 14. There may be a delay however, between the sort trigger delivered to the movable member 110 compared to the trigger for optical camera 160. This delay may give the target particle 150 a chance to move into the sort channel 122, and within the field of view of the optical camera 160.

The optical camera 160 may be configured to generate repeated images of the same field view as triggered by the controller signal just described. These images may be overlaid to show the sequence and time evolution of the field of view of the optical camera 160. Accordingly, as multiple target particles are sorted by particle manipulation stage 10, this plurality of target particles will show appear in the field of view of the optical camera 160. Thus, the output of the optical camera 160 may show multiple particles within the image, and the particles may be clustered in a particular location within the image. The location of this cluster of target particles may be an indication of the relative precision of the timing of the sort pulse relative to detection of fluorescence of the target particle 150 in the detection region 101. The distribution of particles in the channel may be indicative of the variability of particle speed and location, within the flow, or variability in the fluid flow itself, for example.

The geometric center of the cluster is referred to herein as the "locus" of particles within the field of view. The locus may alternatively be understood as the center of the circle which includes most or all of the detected and sorted particles. If the locus appears in the downstream edge of the field of view of optical camera 160, it may be an indication that the sort trigger is somewhat late. In other words, the position of the locus may be an indication that the timing between the detection of the particles by the laser interrogation region 101, and the opening of the sort gate 110, maybe slightly too early or slightly too late. Accordingly, by analyzing the locus of the target particles in the field of view of the optical him a 160, the timing between the detection and sorting operations may be optimized. This may improve at least the purity and/or the yield of the particle manipulation system 100. Accordingly, the particle manipulation system with optical confirmation may be capable of optimizing itself under computer control, that is the system maybe "self-aware". With no other operator intervention, the system may be able to optimize its various parameters including sort gate timing, sort gate width, laser power and positioning, etc., based on the sequence of images captured by the optical camera and analyzed by the computer.

The particle manipulation system may use a camera to image the target particles and a controller to determine the locus of the particles within a field of view of the camera, and the controller may adjust sort gate timing thereby.

Figure 11:
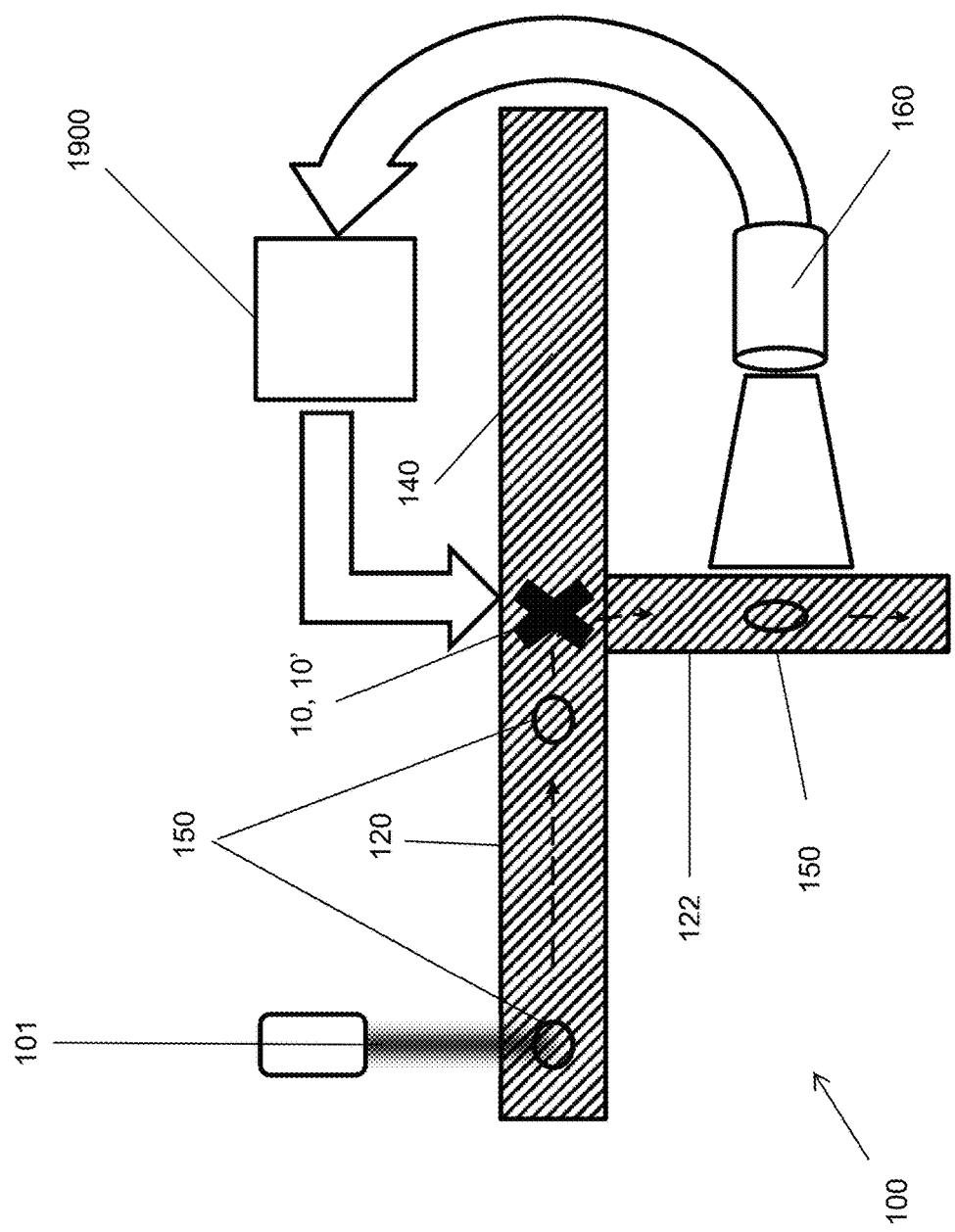
FIG. 11 is a simplified schematic plan view of the microfabricated particle manipulation system with camera confirmation showing the feedback loop between the camera and the controller to control the gate timing of the microfabricated particle manipulation system.

Accordingly, the particle manipulation system with camera confirmation 100 may be used in a feedback loop as illustrated in FIG. 11. FIG. 11 shows the laser interrogation region 101 disposed in the input channel 120 which branches at the particle manipulation stage 10 into the waste channel 140 and sort channel 122. As before, the plurality of target particles 150 may be flowing in the input channel 120 and may be diverted by the particle manipulation stage 10 when the fluorescent signal is detected. The target particle 150 then flows through the field of view of the optical camera 160 which takes an image of the passing target particle 150. By overlaying the plurality of images taken by the optical camera, and analyzed by the controller 1900

(FIG. 14), the system may find the locus of particles within the field of view. The controller 1900 may then make adjustments to the sort gate timing relative to the laser detection, in order to optimize either the purity, or the yield, of the sorted product.

This feedback loop is shown qualitatively and FIG. 11 as the arrows connecting the optical camera 160 to the controller 1900, and the controller 1900 to the movable member 110.

Figure 12:
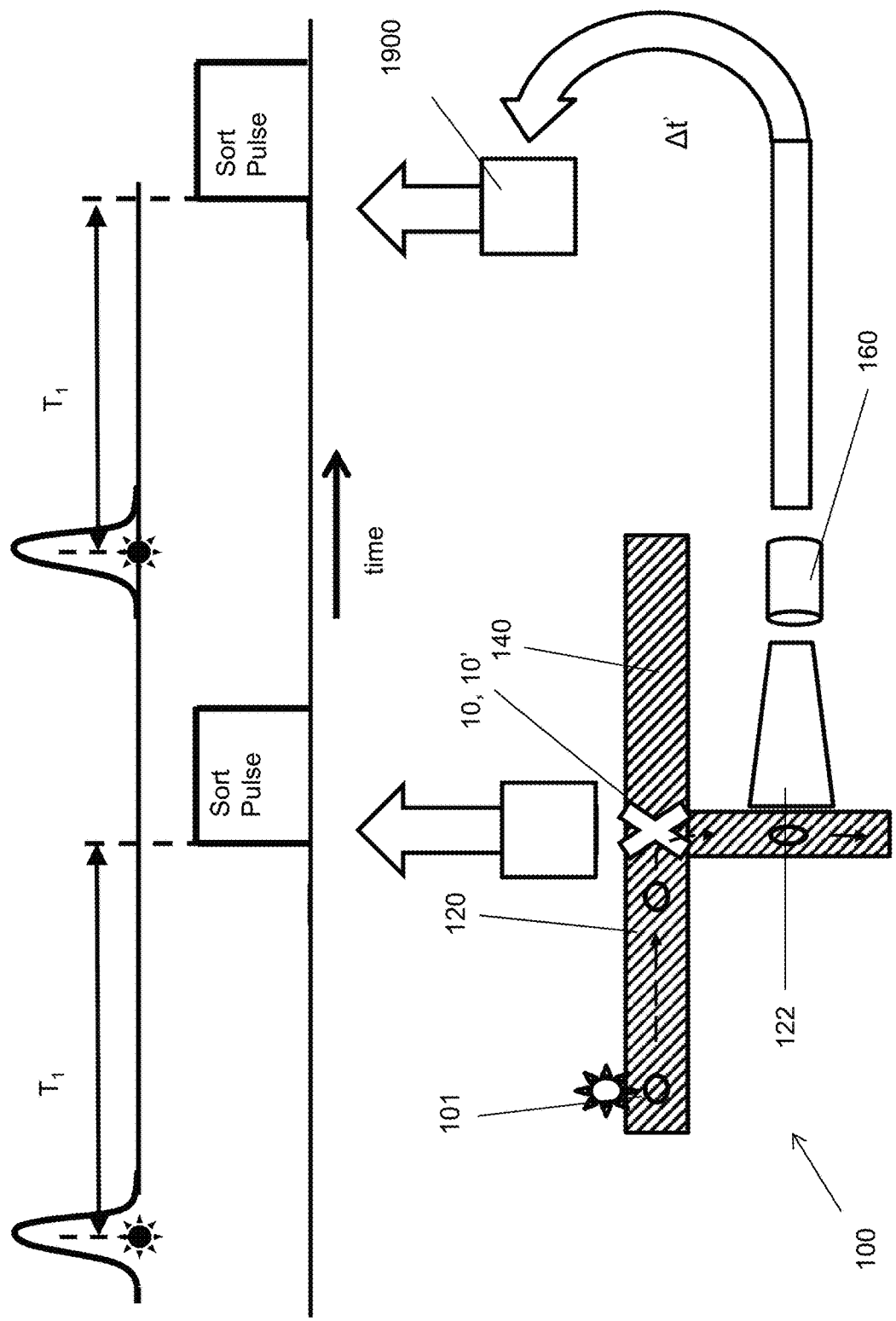
FIG. 12 is the simplified illustration of the feedback loop mechanism shown in FIG. 11.

Normal operation of the system 100 is depicted in FIG. 12. In FIG. 12, the controller regularly puts out a sort pulse in response to the detection of a target particle in the laser interrogation region 101. These pulses are shown on the horizontal axis in FIG. 12. Coincidentally, the optical camera 160 collects overlaid images of the target particles passing through its field of view in the sort channel 122. The data is collected and analyzed by the controller 1900, and adjustments are made to the operating parameters.

Figure 13:
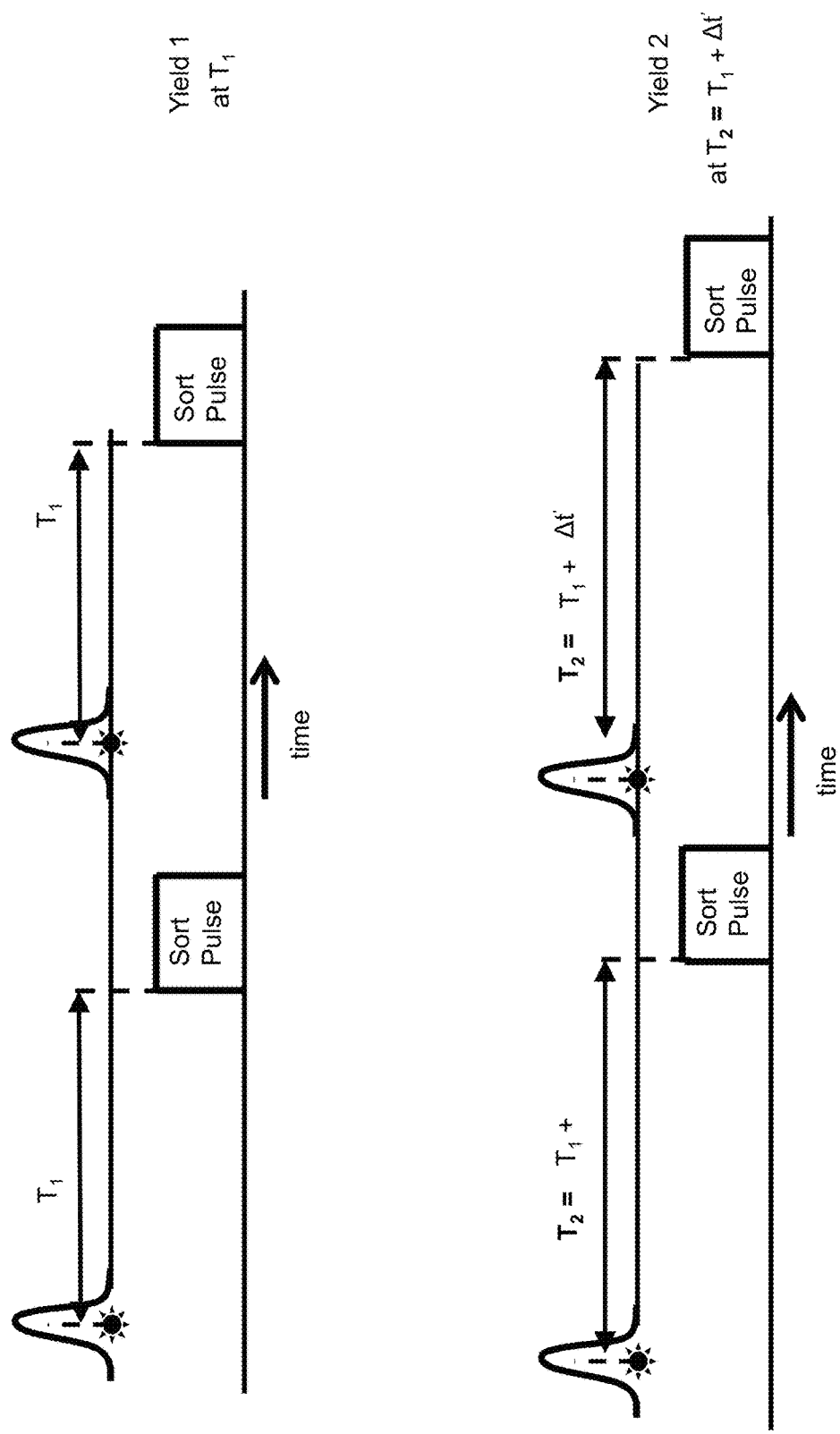
FIG. 13 is the simplified the illustration of an optimization routine involving trigger timing, and the camera confirmation.

The results of the closing of this feedback loop are illustrated in FIG. 13. When the controller, or human operator, analyzes the locus of particles appearing in the field of view of the optical camera 160, a determination may be made that the locus is not placed accurately enough, or is shifted to an edge of the field of view, and that an improvement may be made. In this case, the controller, or an operator, may alter the timing between the laser detection and sort trigger. Before this adjustment is made, the controller may put out a sort trigger at a time T=T1, that is, at a time T1 after the identification of the target particle by the laser interrogation region 101. The operation of the system in this mode will generate sorted population with a yield of some percent, and a purity of another percent. Upon a determination that this yield, or purity, may be improved, the controller 1900 may alter the pulse timing between the detection of the target particle, and the generation of the sort trigger pulse. The controller may determine that this delay should be increased from T=T1, to T=T1+ΔT. This new value is then sent to the movable member 110 at a time T=T1+ΔT. This may result in a relocation of locus of the target particles within the field of view, and improvement in either yield, or purity, or both. The situation is shown qualitatively in FIG. 13.

FIG. 14 is a system-level view showing, among other things, an exemplary layout and connections between the various components of a particle manipulation system 1000 using camera confirmation. The microfabricated particle manipulation device 10 or 10' with camera confirmation 100 may be used in a particle manipulation system 1000 and enclosed in a housing containing the components shown in FIG. 14. The MEMS particle manipulation devices 10 or 10' may be enclosed in a plastic, disposable cartridge which may be inserted into the system 1000. The insertion area may be a movable stage with mechanisms available for fine positioning of the particle manipulation device 10 or 10' and associated microfluidic channels against one or more data, which orient and position the detection region and particle manipulation device 10 or 10' with respect to a set of collection optics 1100. If finer positioning is required, the inlet stage may also be a translation stage, which adjusts the positioning based on observation of the location of the movable member 110 relative to a datum.

A camera confirmation system 1600 may also be included in the particle manipulation system 1000 as show schematically in FIG. 14. It should be understood that although FIG. 14 shows a particle sorting system 1000 which uses a single laser source 1400, multiple light sources, multiple detection optics and multiple channels may also be used. The camera system 1600 may be analogous or equivalent to the camera system 160 shown in the previous figures.

The embodiment shown in FIG. 14 may be based on a FACS-type detection mechanism, wherein one or more lasers 1400 impinges on the sample inlet channel 120 as described above. The relative amount of light may be monitored by a computer 1900. The computer 1900 may then generate a control signal that controls the force-generating means or electromagnet 500. Upon receipt of a fluorescence signal from a target particle, the controller 1900 may output a sort trigger that causes the electromagnet 500 to be energized, thus moving the movable member 110 into the sort position shown in FIG. 7b. The movable member thus diverts the target particle from the input channel 120 into the sort channel 122 rather than the waste channel 140. This is normal operation of the microfabrication particle sorting system 1000. The controller 1900 may generate a camera trigger (as well as a sort trigger) based on the detection of this fluorescence signal.

The other optical components in particle manipulation system 1000 may include a beamsplitter 1500 and multiple color detectors 1300. The beam splitter 1500 may reflect the incoming light from laser 1400 onto the MEMS manipulation device 10.

The output of detectors 1300 may be analyzed by the controller 1900 and compared to a threshold in normal operation.

Accordingly, the particle manipulation system may include a particle manipulation stage and a sample stream in a microfluidic inlet channel, an optical interrogation device upstream of the particle manipulation stage which identifies target particles, and an optical confirmation device downstream of the particle manipulation stage, wherein the optical confirmation device uses a camera to determine the presence or absence of a target particle.

In one embodiment, the MEMS particle manipulation system 1000 may be used in conjunction with one or more additional downstream cameras 160, wherein the additional cameras are used to confirm the effectiveness or accuracy of a manipulation stage in manipulating a stream of particles. The downstream evaluation by camera, as described above, may occur beyond the sorting stage 10 or 10' and may allow the operator to measure one event number (e.g. the captured event rate post-sort) divided by another event number (e.g. the initial event rate pre-sort) for individual particle types, and to feedback to adjust initial interrogation parameters (e.g. such as x, y, z position and also "open window" length in time) based on this ratio. This method may thus be used to optimize the yield or accuracy of the system 1000.

Alternatively, the operator could measure the event rate post-sort of target cells, divided by total event rate post-sort feedback to adjust initial laser interrogation parameters such as x, y, z position and also "open window" length in time, in order to optimize the purity of the sorting system 1000. These sorting parameters may be adjusted by changing control signal 2000 which is sent by computer 1900 to electromagnet 500, or by changing the optical detection parameters or by changing the laser control signals, as shown in FIG. 14. In any case, the camera system 1600 may be used in conjunction with controller 1900 to improve or optimize the performance of the system with respect to at least one measured parameter.

Accordingly, the particle manipulation system may image the target particles with the camera, determine the locus of the particles within a field of view of the camera with a controller, and adjust a sorting parameter. One such sorting parameter is the timing of the sort gate, but other parameters may include at least one of laser fluorescent pulse shape, width, magnitude or duration, laser intensity, optical alignment or focusing, gate duration, and so forth. These parameters may be optimized with respect to purity, yield, or some other measured output of the system 100.

Figure 15:
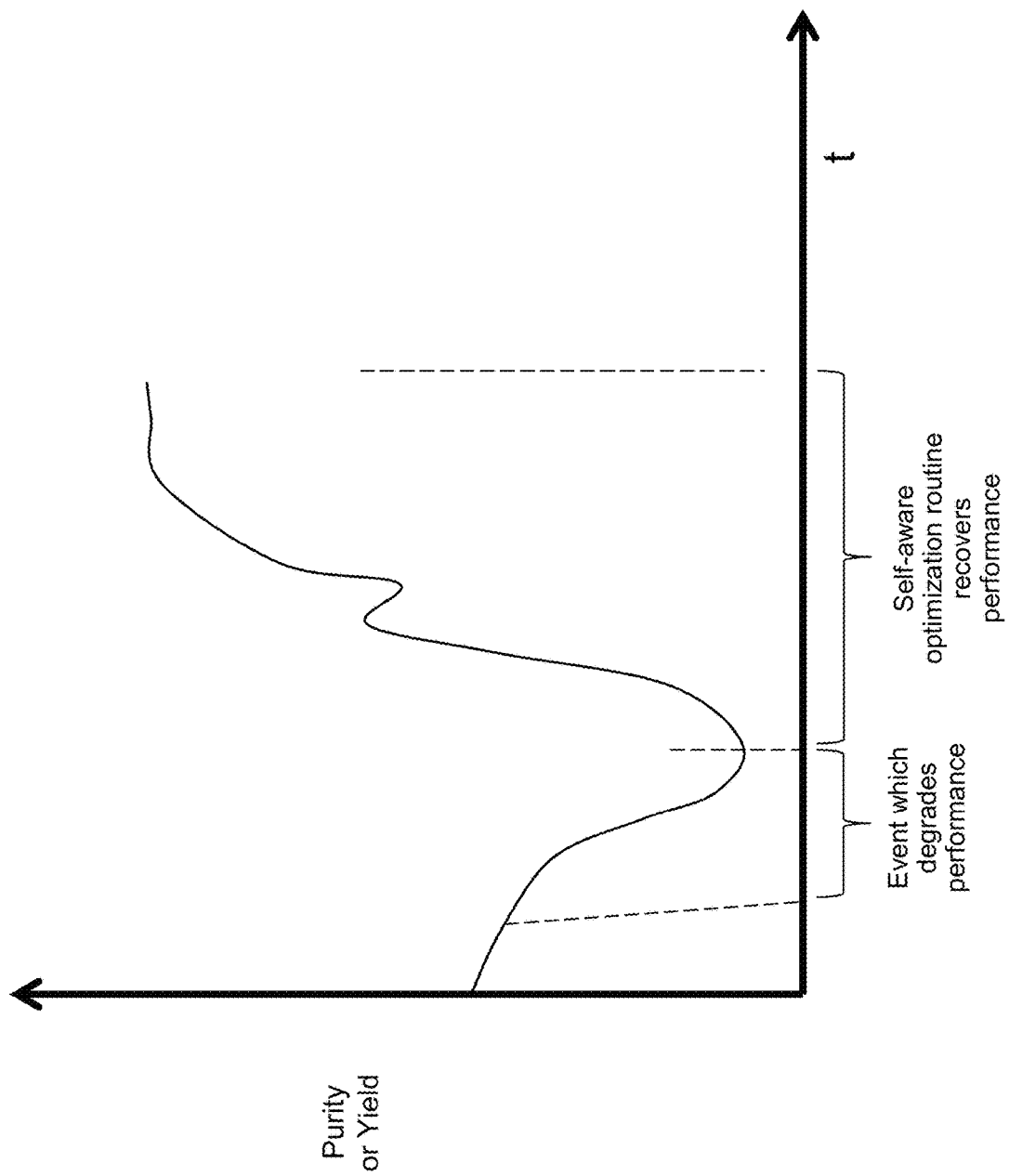
FIG. 15 is a representation of the effectiveness of the camera confirmation system and bringing the particle manipulation system to affective operating mode, after an event which degraded performance.

FIG. 15 is a plot of the purity or yield versus timing of the sort pulse trigger. This plot illustrates the effect on the yield or purity of some event which throws the system out of this optimized operating space. The event may be a shock, a power surge, a sudden change in temperature, for example. The event may occur on the timeline shown in FIG. 15. The effect of the event is to cause a deterioration in the purity and/or yield of the particle manipulation system 1000. As the system becomes aware of the deterioration in performance, it will adjust the timing of the sort gate to find the direction of improvement. The self-aware system may continue to adjust the sort gate until adequate improvement is achieved. This improvement is shown as the second indicated period in FIG. 15. Accordingly, the system may be self-optimizing ("self-aware"), that is, requiring no human intervention in order to find the optimum set of parameters under which the device can operate. When any of these parameters becomes less than optimal, the software system may adjust the parameters until the optimum operation is recovered.

Accordingly, by using the self-aware systems and methods described here, the particle manipulation system 1000 can monitor itself for a malfunction situation, or take corrective action after a disruptive event. For example, in the event that either the purity or the yield drops anomalously, the self-aware system 1000 may declare a malfunction to have occurred, and invoke the recovery algorithm. Alternatively, the camera system 160 can be positioned to view the movable member 110, and detect a clog or a jam of the movable member 160. In any case, a recovery algorithm may be invoked. This recovery algorithm may include, for example, sending a pulse train to the electromagnet 500, wherein the pulse train drives the movable member 110 at or near its resonant frequency. Accordingly, this recovery algorithm may include vibrating the movable member 110 at or near is resonant frequency, in order to grind the piece of debris into smaller pieces, at which point it is swept away by the fluid stream, and freeing the movable member. The frequency could be up from about 1 khz up to about 100 khz. This vibration may shake both the actuator and any material clinging to it, and may also propagate via liquid flow to surrounding areas. The vibration may thus be akin to an ultrasonic cleaning event, and may last for a second or so to clear the jam. This recovery algorithm is described in further detail in co-pending U.S. patent application Ser. No. 15/159, 841, filed May 20, 2016 and assigned to the same assignee as the present invention.

The particle manipulation system with camera confirmation may be used to detect the approaching end of sample condition, wherein the input channel may have no or reduced flow. The particle manipulation system may the invoke an algorithm to reverse the flow in the channels, in order to keep the surfaces wet. These algorithms are discussed in further detail in pending U.S. Pat. No. 9,168,568, issued Oct. 27, 2015 and U.S. Pat. No. 9,360,164 issued Jun. 7, 2016. These patents are assigned to the same assignee as the present invention.

A number of embodiments are envisioned for the functioning of the camera confirmation 1600. In one embodiment, the camera confirmation 1600 is not actively invoked by an operator, but instead is invoked regularly at intervals, as a maintenance or preventive measure. In other words, the optical confirmation system described above may be implemented in a full-time mode, i.e. the operating parameters are adjusted in a continuous fashion.

In the full-time mode, measurements may be taken constantly, and the system may give a continuous measurement of purity, yield, locus position running in feedback mode, etc. In this mode, there may be "dead-time" lockout, so that after a sort, another sort cannot occur before the dead-time is complete. This prevents another particle from showing up in the sort and altering the self-aware measurement. Accordingly, operating the self-aware system full time or constantly may have an overhead penalty, and reduce the speed of sorting or the time required to complete a sample.

The situation may also arise, wherein multiple numbers or multiple types of particles are targeted for sorting. In this situation, the camera may be used to confirm that the multiple target particles have correctly been sorted.

Alternatively, the camera confirmation may by intermittent, such that results are audited periodically, and optimization of parameters undertaken when needed. In the audit mode, the purity and yield may be monitored while various parameters are varied around the operating point. For example, the gate timing can be lengthened or shortened to verify that the optimum gate timing is in use. This audit procedure may be invoked as a function of time, for example twice daily, or as a function of the number of events or sort of particles, or as a function of the volume of fluid passing through the device 1000. In any event, the performance of the system 1000 may be evaluated periodically from time to time, and verification of the optimized parameter set can be performed.

For example, the system 100 may switch between full time and audit mode. When the system recognizes when the sort rate is high enough to lose a significant number of sorts (if in full-time mode), and switches to making self-aware measurements during a measurement audit time period, which is a fraction of the total sorting time. An insignificant number of sorts may be lost, due to the dead-time lockout, i.e. the period during which the computer is analyzing images.

The images generated be the camera 160 may be analyzed to determine the statistical arrival times of the particles in the sort channel. By fitting these results to Poisson statistics, the system can be optimized to minimize the lost sorts. For some sorting rates, the system should be able to avoid any lost sorts. This may either require a longer time between optical detection and the sort region, or the ability to reject some of the images.

As described above, the optical camera may be triggered by the same signal which triggers the movable member to perform the sort. That is, the optical camera maybe triggered by the detection of fluorescence. In order to further specify exactly when the optical camera acquires an image, a strobe light may be applied to the viewing area as was shown in FIGS. 7*a* and 7*b*. The strobe light will effectively freeze the motion of the member 110 such that it appears to be stationary in the images. Strobing the camera position may improve the signal to noise of the data collected, and in particular, it may improve the measurement of the positioning of the particles within the locus.

Other optical microscopy techniques may also be brought to bear on the optical confirmation system described above. For example, dark field microscopy, the technique well known in the optical microscope field, for enhancing the contrast especially for small, generally translucent particles. These techniques may be brought to bear on the optical camera confirmation method described above. That is, the camera may be operated in the dark field mode, thereby enhancing the contrast of small, translucent particles. Phase contrast may also be used to observe cell changes.

The particle manipulation system with camera confirmation may also make use of differential interferometric (Nomarski) microscopy. Accordingly, the camera may image the target particles using at least one of dark field lighting, phase contrast and strobe lighting. Using phase and Nomarksi methods may provide more information about the cells, including their morphology, viability, complexity and detail of components making up the particles.

The camera system may detect more than just the presence or absences of a target cell 150. It may also image the shape of the cells, thereby establishing physical integrity and viability. The valve timing may then be optimized, via the feedback loop shown in FIG. 12, the cell shape for example. This data may speak to the physical condition of the cells, and may be of interest to customers and medical professionals. Accordingly, the particle manipulation system 1000 may be used to gauge cell health.

In addition to the usual scatter or "dot" plots, the imaging data may be used to construct 4D plots, 2D fluorescent and 2D positional plots for example. The mapping function between plots can give more information about the characteristics of the sorted cells. For example, if cell had more inertia because of larger size or higher density, it would be sorted but end up in a different place within the locus than a lower inertia cell. So the mapping would contain information on the inertia (gravimetric density). The particle manipulating system 1000 may be programmed to sort using such information.

The optical confirmation system 1000 just described may be suitable for measuring a number of different characteristics of the particles in the flow channels. For example, the images may provide information us to the granularity, the density, the gravimetric density, the deformability, etc. in addition to optical properties. These measurements may be used to optimize or enhance any number of parameters using the sorting algorithm, such as gate timing, gate length, laser intensity, detector parameters. etc. Accordingly, The particle manipulation system may image the target particles to display the deformability of the target particles. The particle manipulation system may image the target particles and display data directed to at least one of cell health, deformability, granularity and gravimetric density.

The optical confirmation system described here may also be used with a single cell dispensing system as described in Ser. No. 14/275,974, filed May 13, 2014. Using the camera confirmation techniques, a single target cell may be isolated and dispensed into a quantity of buffer fluid. The system may also allow single cell dispensation of the target particle into a separate receptacle.

Accordingly, in addition to cytometry or cell counting, the particle manipulation system with camera confirmation 1000 may be used for other applications, including sperm cell orientation, single cell dispensation, measure cell deformability so as to get a time constant for deformation and recovery. The particle manipulation system with camera confirmation may image sperm cells in the sample stream and display their orientation.

A method is envisioned for manipulating target particles flowing in a sample stream based on the system described above. The method may include providing a particle manipulation stage in a microfluidic channel, identifying target particles with an optical interrogation device upstream of the particle manipulation stage; and using a camera as an optical confirmation device downstream of the particle manipulation stage, to determine the presence or absence of a target particle. The method may further comprise an operational feedback loop. This feedback loop may include the following steps: determining a locus of target particles in a field of view; and adjusting a sorting parameter based on the locus. This operational feedback loop may be invoked at least one of continuously, intermittently, and at predefined intervals.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. Accordingly, the exemplary implementations set forth above, are intended to be illustrative, not limiting.

What is claimed is:
1. A particle manipulation system, comprising:
   a plurality of microfluidic channels including an microfluidic input channel, a sort channel and a waste channel formed in a plane, and wherein a sample stream flows in the input channel, wherein the sample stream including target particles and non-target material;
   a microfabricated particle sorting device disposed at a junction of the input channel, the sort channel and the waste channel, wherein the microfabricated particle sorting device moves in a plane to sort target particles by directing the target particles into the sort channel as sorted particles; wherein
   an optical interrogation device upstream of the microfabricated particle sorting device which identifies the target particles; and
   an optical confirmation device downstream of the microfabricated particle sorting device, wherein the optical confirmation device comprises a camera and a controller to determine the presence or absence of the sorted particles, wherein the controller implements a feedback loop using the camera and wherein the controller is programmed to adjust a sorting parameter based on a locus of the particles within a field of view of the camera, such that the particle manipulation system is self aware.
2. The particle manipulation system of claim 1, wherein the feedback loop is invoked at least one of continuously and intermittently.
3. The particle manipulation system of claim 2, further comprising:
   a sheath fluid inlet in fluid communication with the microfluidic input channel; and
   a focusing element coupled to the sheath fluid inlet, which is configured to urge the target particles into a particular portion of the microfluidic input channel.
4. The micromechanical particle manipulation system of claim 3, wherein focusing element comprises a z-focus channel, wherein the z-focus channel curves in an arc of about 180 degree from the sheath fluid inlet, and urges the target particles into substantially a single plane.
5. The micromechanical particle manipulation system of claim 3, wherein the z-focus channel has a radius of curvature of at least about 100 microns and less than about 500 microns, and wherein the microfluidic input channel and z-focus channel both have characteristic dimensions of about 50 microns.
6. The particle manipulation system of claim 3, wherein the focusing element includes an acoustic focusing element, which urges the target particles using sound waves.

7. The particle manipulation system of claim 1, wherein the camera images the target particles using at least one of dark field lighting, differential interferometric and strobe lighting.

8. The particle manipulation system of claim 1, wherein the locus is defined as a center of a circle which includes most of the sorted particles.

9. The particle manipulation system of claim 1, wherein the camera images the target particles to allow single cell dispensation of the target particle into a separate receptacle.

10. The particle manipulation system of claim 1, wherein the camera images the target particles to display deformability of the target particles.

11. The particle manipulation system of claim 1, wherein the camera images the target particles and displays data directed to at least one of cell health, deformability, granularity and gravimetric density.

12. The particle manipulation system of claim 1, wherein the controller detects a malfunction in the particle sorting device, and initiates a recovery algorithm.

13. The particle manipulation system of claim 1, wherein the camera images the target particles and a controller is programmed to analyze the images received from the camera to determine the locus of the particles within a field of view of the camera, and wherein the controller is programmed to adjust a sorting parameter thereby based on the analysis of the images.

14. The particle manipulation system of claim 13, wherein the sorting parameter is at least one of the timing of the sort gate, laser fluorescent pulse shape, width, magnitude or duration, laser intensity, optical alignment or focusing, gate duration.

15. A particle manipulation system, comprising:
a microfabricated particle sorting device, wherein the microfabricated particle sorting device moves in a plane, and is disposed in a microfluidic channel through which a sample stream flows, wherein the microfluidic channel is also formed in the plane, and wherein the sample stream includes target particles and non-target material;
an optical interrogation device upstream of the microfabricated particle sorting device which identifies target particles; and
an optical confirmation device downstream of the microfabricated particle sorting device, wherein the optical confirmation device comprises a camera and a controller to determine the presence or absence of a target particle, wherein the controller implements a feedback loop which adjusts a sorting parameter based on an image from the camera;
a sheath fluid inlet in fluid communication with the microfluidic input channel; and
a focusing element coupled to the sheath fluid inlet, which is configured to urge the target particles into a particular portion of the microfluidic input channel, wherein the focusing element is disposed in the same plane as the microfabricated particle sorting device.

16. A particle manipulation system, comprising:
a microfabricated particle sorting device, wherein the microfabricated particle sorting device moves in a plane, and is disposed in a microfluidic channel through which a sample stream flows, wherein the microfluidic channel is also formed in the plane, and wherein the sample stream includes target particles and non-target material;
an optical interrogation device upstream of the microfabricated particle sorting device which identifies target particles; and
an optical confirmation device downstream of the microfabricated particle sorting device, wherein the optical confirmation device comprises a camera to determine the presence or absence of a target particle, wherein the camera is used in a feedback loop by a controller which adjusts a sorting parameter based on a locus of the particles within a field of view of the camera,
and wherein the microfabricated particle sorting device further comprises a sort output channel into which the microfabricated member diverts the target particles and a waste output channel into which the non-target material flows, and wherein the flow in waste output channel is substantially orthogonal to the plane, and wherein the waste output channel is located directly below at least a portion of the microfabricated particle sorting device over at least a portion of its motion.

17. A method for manipulating a target particle, comprising:
providing a microfabricated particle sorting device, wherein the microfabricated particle sorting device moves in a plane, and is disposed in a microfluidic channel through which a sample stream flows, wherein the microfluidic channel is also formed in the plane, and wherein the sample stream includes target particles and non-target material;
identifying target particles with an optical interrogation device upstream of the particle manipulation stage; and
using a camera as an optical confirmation device downstream of the particle manipulation stage, to determine the presence or absence of a target particle, wherein a controller adjusts a sorting parameter based on a locus of the particles within a field of view of the camera.

18. The method of claim 17, further comprising an operational feedback loop which comprises:
determining the locus of particles in a field of view; and
adjusting a sorting parameter based on the locus.

19. The method of claim 18, wherein the operational feedback loop is invoked at least one of continuously and intermittently.

* * * * *